(12) United States Patent
Chen et al.

(10) Patent No.: US 11,344,548 B2
(45) Date of Patent: May 31, 2022

(54) ANALOGS OF 3,5-DIHYDROXYPENTANOATE FOR BONE FORMATION

(71) Applicants: KAOHSIUNG MEDICAL UNIVERSITY, Kaohsiung (TW); Alice Y Huang, Wallingford, CT (US)

(72) Inventors: Hui-Ting Chen, Kaohsiung (TW); Kuang-Chan Hsieh, Kaohsiung (TW); Chai-Lin Kao, Kaohsiung (TW); Je-Ken Chang, Kaohsiung (TW); Mei-Ling Ho, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 1329 days.

(21) Appl. No.: 15/557,360

(22) PCT Filed: Oct. 8, 2015

(86) PCT No.: PCT/US2015/054692
§ 371 (c)(1),
(2) Date: Sep. 11, 2017

(87) PCT Pub. No.: WO2016/130181
PCT Pub. Date: Aug. 18, 2016

(65) Prior Publication Data
US 2021/0322411 A1    Oct. 21, 2021

(30) Foreign Application Priority Data

Feb. 11, 2015 (TW) ................... 104104625

(51) Int. Cl.
*A61K 31/505* (2006.01)
*A61K 47/64* (2017.01)
(Continued)

(52) U.S. Cl.
CPC ............ *A61K 31/505* (2013.01); *A61K 31/40* (2013.01); *A61K 31/44* (2013.01); *A61K 31/47* (2013.01);
(Continued)

(58) Field of Classification Search
CPC ........ A61K 31/22; A61K 31/40; A61K 31/44; A61K 31/4418; A61K 31/47;
(Continued)

(56) References Cited

PUBLICATIONS

Anderson (Chem and Biol 10:787-797, 2003), (Year: 2003).*
(Continued)

*Primary Examiner* — Savitha M Rao
(74) *Attorney, Agent, or Firm* — Volpe Koenig

(57) ABSTRACT

A method for treating low bone mineral density associated with osteopenia, osteoporosis, and other diseases is disclosed. The method comprises administrating a composition comprising a 3,5-dihydroxypentanoic acid derivative according to Formula I to a mammal. A compound of 3,5-dihydroxypentanoic acid derivative having a structure according to Formula I or Formula II is also disclosed.

(I)

(Continued)

-continued

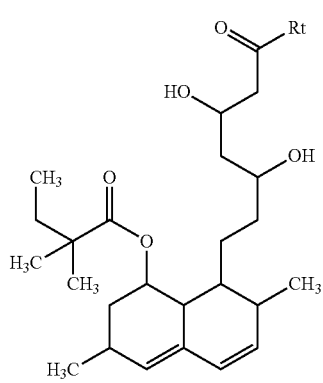
(II)

7 Claims, 14 Drawing Sheets

Specification includes a Sequence Listing.

(51) Int. Cl.
*A61K 31/40* (2006.01)
*A61K 31/44* (2006.01)
*A61K 31/47* (2006.01)
*A61P 19/10* (2006.01)
*A61P 19/08* (2006.01)

(52) U.S. Cl.
CPC .............. *A61K 47/64* (2017.08); *A61P 19/08* (2018.01); *A61P 19/10* (2018.01)

(58) Field of Classification Search
CPC ...... A61K 31/505; A61K 38/10; A61K 47/64; A61P 19/08; A61P 19/10
See application file for complete search history.

(56) References Cited

PUBLICATIONS

Thiel (Nature Biotechnol 2:513-519, 2004), (Year: 2004).*
Jeon et al. (journal of periodontology, vol. 79, issue 8, pp. 1457-1464) (Year: 2008).*
Hsieh et al (Organic Letters, 2014, 16, 4376-4379) (Year: 2014).*
CN 10215297 English translation (Year: 2008).*

* cited by examiner

SEQUENCE LISTING

<160> NUMBER OF SEQ ID NOS: 28

<210> SEQ ID NO 1
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 1

```
Thr Met Arg Asn Pro Ile Thr Ser Leu Ile Ser Val
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 2

Leu Leu Ala Asp Thr Thr His His Arg Pro Trp Thr Gly Gly Gly Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 3

Lys Glu Ile Pro Pro Ile Pro Leu Leu Ala Pro Ser Gly Gly Gly Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 4

Asn Asn Val Ser Gln Lys Trp Gln Gln Arg Leu Ile Gly Gly Gly Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 5

Asn Ser Met Ile Ala His Asn Lys Thr Arg Met His Gly Gly Gly Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 6

Gly Ile His Val Pro Trp Met Pro Pro Val Ala Phe Gly Gly Gly Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 7
```

```
Gln Arg Ser Trp Thr Leu Asp Ser Ala Leu Ser Met Gly Gly Glu Ser
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 8

```
Ser Gly His Gln Leu Leu Leu Asn Lys Met Pro Asn Gly Gly Gly Ser
1               5                   10                  15
```

<210> SEQ ID NO 9
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 9

```
Ser Ser Thr Leu Lys Thr Phe Phe Gly Phe Pro Asp Gly Gly Gly Ser
1               5                   10                  15
```

<210> SEQ ID NO 10
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 10

```
Asp Ser Ser Asn Pro Ile Phe Trp Arg Pro Ser Ser Gly Gly Gly Ser
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 11

```
Asn Thr Ser His Leu Arg Val Lys Leu Pro Thr Pro Gly Gly Gly Ser
1               5                   10                  15
```

<210> SEQ ID NO 12
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 12

```
Ser Gly His Gln Leu Leu Leu Asn Lys Met Pro Asn Gly Gly Gly Ser
1               5                   10                  15
```

<210> SEQ ID NO 13
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 13

Ala Thr Trp Ser His His Leu Ser Ser Ala Gly Leu Gly Gly Gly Ser

<210> SEQ ID NO 14
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 14

Ser Tyr Ser Gln Met Asp Pro Pro Arg Ser Leu Pro Gly Gly Gly Ser
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 15

Thr Met Arg Asn Pro Ile Thr Ser Leu Ile Ser Val
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 16

Leu Leu Ala Asp Thr Thr His His Arg Pro Trp Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 17

Lys Glu Ile Pro Pro Ile Pro Leu Leu Ala Pro Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 18

Asn Asn Val Ser Gln Lys Trp Gln Gln Arg Leu Ile
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 19

Asn Ser Met Ile Ala His Asn Lys Thr Arg Met His
1               5                   10

```
<210> SEQ ID NO 20
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 20

Gly Ile His Val Pro Trp Met Pro Pro Val Ala Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 21

Gln Arg Ser Trp Thr Leu Asp Ser Ala Leu Ser Met
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 22

Ser Gly His Gln Leu Leu Leu Asn Lys Met Pro Asn
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 23

Ser Ser Thr Leu Lys Thr Phe Phe Gly Phe Pro Asp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 24

Asp Ser Ser Asn Pro Ile Phe Trp Arg Pro Ser Ser
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 25

Asn Tyr Ser His Leu Arg Val Lys Leu Pro Thr Pro
1               5                   10
```

```
<210> SEQ ID NO 26
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 26

Ser Gly His Gln Leu Leu Leu Asn Lys Met Pro Asn
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Bone-targeting peptide

<400> SEQUENCE: 27

Ala Thr Trp Ser His His Leu Ser Ser Ala Gly Leu
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Bone-targeting peptide

<400> SEQUENCE: 28

Ser Tyr Ser Gln Met Asp Pro Pro Arg Ser Leu Pro Gly Gly Gly Ser
1               5                   10                  15
```

ANALOGS OF 3,5-DIHYDROXYPENTANOATE FOR BONE FORMATION

CROSS-REFERENCE TO RELATED APPLICATION AND CLAIM OF PRIORITY

The application claims the benefit of Taiwan Patent Application No. 104104625, filed on Feb. 11, 2015, at the Taiwan Intellectual Property Office, the disclosures of which are incorporated herein in their entirety by reference.

FIELD OF THE INVENTION

The present invention is related to 3,5-dihydroxypentanoate derivatives promoting bone formation and the method thereof, and more particularly, their bone formation effect is independent to the mevalonate (MVA) pathway.

BACKGROUND OF THE INVENTION

The bone anabolic activity of statins is independent to the pathway for lipid synthesis, alternatively relates to their pleiotropic effects. 3,5-dihydroxypentanoic acid that statins including is considered to mimic the substrate of 3-hydroxy-3-methyl glutaryl-coenzyme A reductase (HMG-CoA reductase) in MVA pathway to inhibit lipid synthesis, and thus lead statins to be powerful cholesterol lowering agents. The effect of the MVA pathway to the bone has been proven to modulate the activity of osteoclast to inhibit bone resorption. The known inhibitor of HMG-CoA reductase, statin, have been found it not only inhibit bone resorption and also increase osteoblast activity to induce bone formation through other alternative pathways from MVA pathways. However, it has not been discovered the required structure of statins for bone formation, and also important to develop a strategy to reduce the distribution of statins in liver tissue and increase the bone tissue affinity thereof. These lessons need to be taken to remove the obstacle in the front of concerning the development that statins act as bone anabolic agents. HMG-CoA reductase is mainly distributed in the liver and contributes to lipid synthesis. Highly effective lowering lipid compounds need to have high affinity to HMG-CoA reductase in the liver and high liver cell selectivity. Therefore, if the distribution of HMG-CoA reductase in the bone tissue will be raised, to reduce the inhibitory activity of HMG-CoA reductase may be a strategy to prevent such compounds from concentrating or functioning in the liver.

Statins have been reported currently to be a potential therapy for treating bone mass disease. They have promising benefits to promote bone mass increase in animal experiments especially by administration. However, whether randomized controlled trials or systematic reviews were applied, statins which were administered to menopausal women show controversial results in preventing fracture or increasing bone density, and thus it was considered that there is a dispute regarding the effect of whole body administration in a human. Therefore, the essential structure of statins for bone formation has room for discovery, and it is necessary to develop statin derivatives with bone selectivity, and they can be used for the whole body.

In order to overcome the drawbacks in the prior art, derivatives of 3,5-dihydroxypentanoate for bone formation are disclosed. The particular design in the present invention not only solves the problems described above, but also easy to implement. Thus, the present invention has utility for industry.

SUMMARY OF THE INVENTION

In accordance with one aspect of the present invention, a 3,5-dihydroxypentanoic acid analog according to Formula I is disclosed,

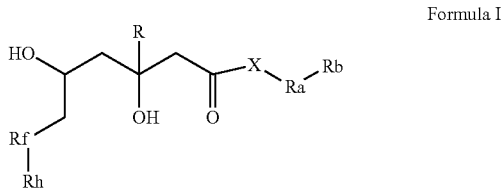

Formula I wherein X is one of nitrogen and carbon;

R is one of hydrogen and $C_1$-$C_4$ alkyl group;

Ra is one group selected from the following groups: (a1) a $C_1$-$C_{10}$ alkyl group, (a2) a substituted $C_1$-$C_{10}$ alkyl group, (a3) a $C_3$-$C_8$ cycloalkyl group, (a4) a substituted $C_3$-$C_8$ cycloalkyl group, (a5) a phenylamino group, (a6) a substituted phenylamino group, (a7) a $C_1$-$C_{10}$ phenyl alkylamino group, (a8) a substituted $C_1$-$C_{10}$ phenyl alkylamino group, (a9) a bisphosphonate, (a10) tetracycline, (a11) an amino acid, (a12) an acidic oligopeptide, (a13) a bone-targeting peptide and (a14) a bone affinity peptide, U-Lys(U)-Lys(U)-Gly-OH, wherein U is one selected from the group consisting of -Lys, -Lys-(Asp-NHAc)$_J$, —NHAc, -Lys-(Asp-)$_K$-NHAc and (Asp-NHAc)$_J$, wherein J is 1 or 2, and K is an integer, 1≤K≤20;

Rb is one selected from the group consisting of hydrogen, a substituted group, an acetyl group and an imaging moiety;

The bond between Rf and Rh are single- or a double bond;

Rh is one selected from the group consisting of compounds represented by Formulae (A), (B), (C), (D), (E) and (F)

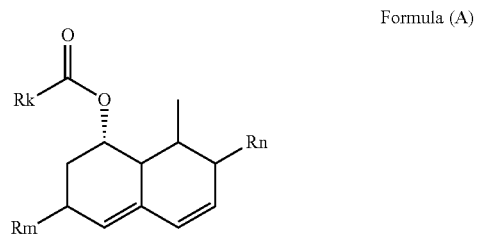

Formula (A)

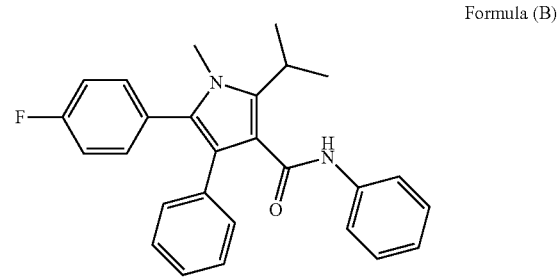

Formula (B)

-continued

Formula (C)

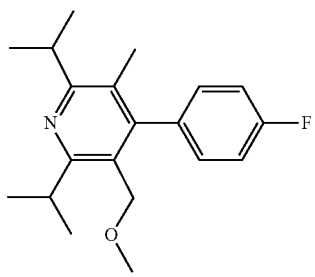

Formula (D)

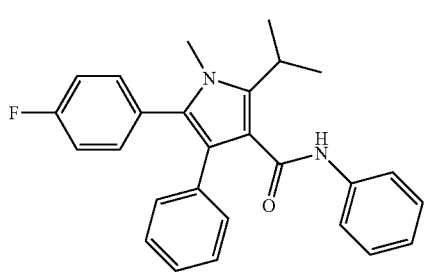

Formula (E)

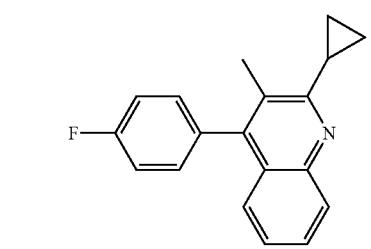

Formula (F)

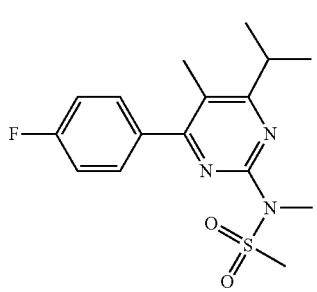

Rk is a $C_1$-$C_5$ alkyl group;
Rm is one of $C_1$-$C_5$ alkyl groups and a hydroxyl group; and
Rn is one of $C_1$-$C_5$ alkyl groups and a hydroxyl group.

According to the present invention, in an appropriate embodiment, the derivative of 3,5-dihydroxypentanoic acid, further includes an imaging moiety, which can be used as a tool in the diagnosis for human or animals. Imaging is achieved by administrating 3,5-dihydroxypentanoic acid derivative.

In accordance with another aspect of the present invention, a method for manufacturing 3,5-dihydroxypentanoic acid derivatives including Formula I by adding additives and excipients to enhance bone mass to treat a disease in vertebrates is disclosed.

In accordance with a further aspect of the present invention, a method for treating a disease of low bone mass is disclosed. The method includes the step of administrating a pharmaceutical composition and/or food composition including a 3,5-dihydroxypentanoic acid derivative according to Formula I to a vertebrate.

In accordance with a further aspect of the present invention, a method for manufacturing 3,5-dihydroxypentanoic acid derivatives, which is provided by solid-phase peptide synthesis (SPPS) through fluorenylmethoxycarbonyl (fmoc) approach is disclosed. The method includes (a) providing Fmoc-Gly-preloaded Wang resin as the starting to cause the lysine to connect thereto; (b) providing amide bond formation to form a conjugate simvastatin acid with an α-amino group of lysine via lactone ring opening; and (c) performing the process at over 100° C. and irradiated by microwave at more than 150 W for 100-minute reaction.

The objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
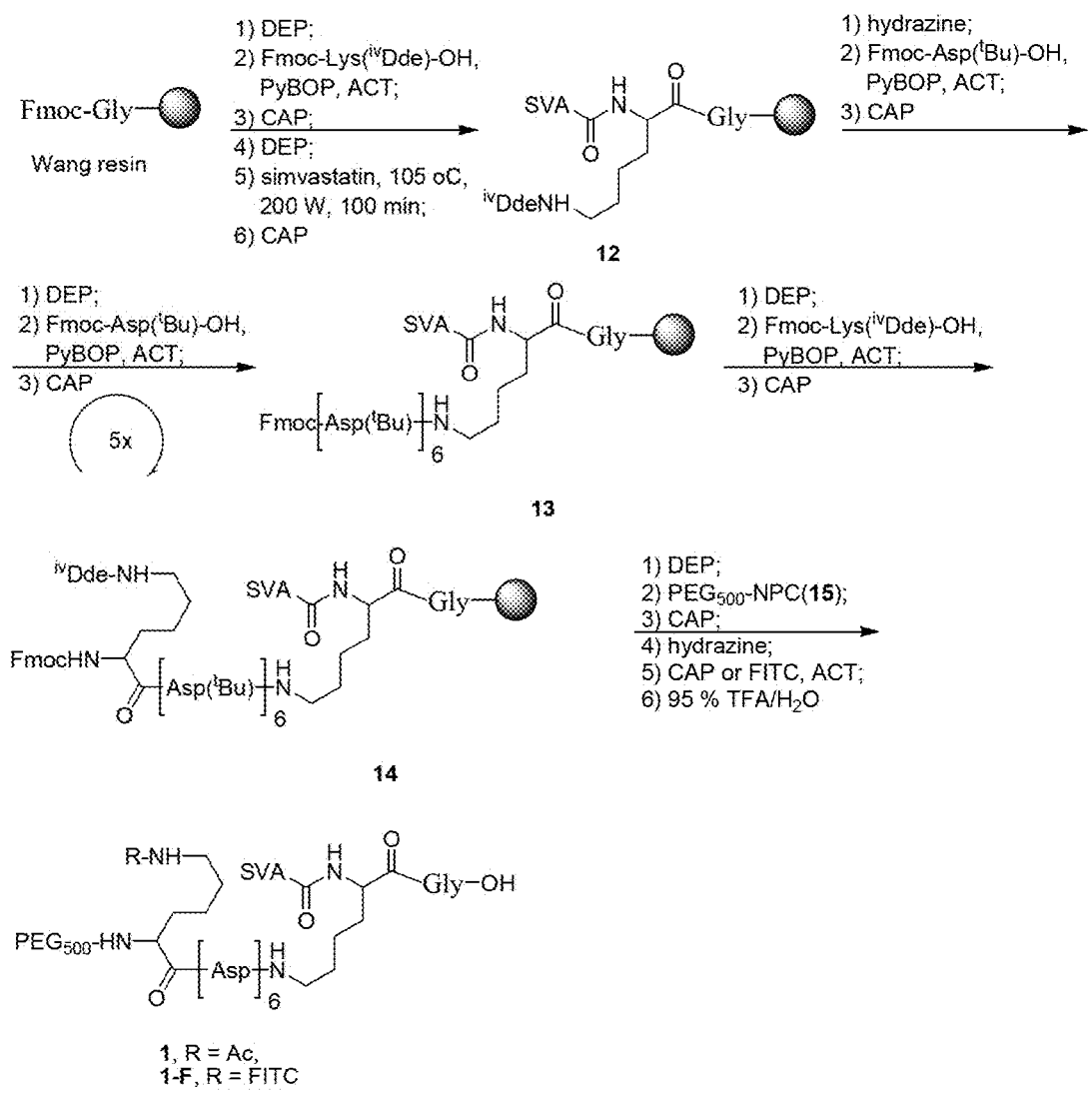
FIG. 1 shows the scheme A of the manufacturing method.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

To achieve the objectives of the above invention, for the dihydroxypentanoate derivatives according to Formula I, Ra is (a2) a substituted $C_1$-$C_{10}$ alkyl group, and the substituted group is one selected from the group consisting of a $C_1$-$C_{10}$ alkyl group, a $C_1$-$C_{10}$ alkoxy group, a $C_1$-$C_5$ alkoxycarbonyl group, a $C_1$-$C_5$ acyloxy group, a $C_3$-$C_8$ cycloalkyl group, a phenyl group and a substituted phenyl group.

Ra is one selected from the group consisting of (a4) a substituted cycloalkyl group with $C_3$-$C_8$, (a6) a substituted phenylamino group and (a8) a substituted phenyl alkylamino group with $C_1$-$C_{10}$, and the substituted group is one selected from the group consisting of an alkyl group with $C_1$-$C_5$, fluorine, chlorine, bromine, iodine, furan, a six-member aromatic ring with at least one oxygen atom, pyrrole and pyridine.

Ra is (a12) acidic oligopeptides and is one selected from the group consisting of -Lys-(Asp)$_m$-Lys-PEG, Asp$_m$ and Glu$_n$, wherein m and n are both integers from 1 to 10, inclusive, each Asp residue is one of D-Asp and L-Asp, and each Glu residue is one of D-Glu and L-Glu.

Ra is (a13) bone-targeting peptide which is one selected from the group consisting of Thr-Met-Arg-Asn-Pro-Ile-Thr-Ser-Leu-Ile-Ser-Val (SEQ ID NO: 1),
Leu-Leu-Ala-Asp-Thr-Thr-His-His-Arg-Pro-Trp-Thr-Gly-Gly-Gly-Ser (SEQ ID NO: 2),
Lys-Glu-Ile-Pro-Pro-Ile-Pro-Leu-Leu-Ala-Pro-Ser-Gly-Gly-Gly-Ser (SEQ ID NO: 3),
Asn-Asn-Val-Ser-Gln-Lys-Trp-Gln-Gln-Arg-Leu-Ile-Gly-Gly-Gly-Ser (SEQ ID NO: 4),
Asn-Ser-Met-Ile-Ala-His-Asn-Lys-Thr-Arg-Met-His-Gly-Gly-Gly-Ser (SEQ ID NO: 5),
Gly-Ile-His-Val-Pro-Trp-Met-Pro-Pro-Val-Ala-Phe-Gly-Gly-Gly-Ser (SEQ ID NO: 6),
Gln-Arg-Ser-Trp-Thr-Leu-Asp-Ser-Ala-Leu-Ser-Met-Gly-Gly-Glu-Ser (SEQ ID NO: 7),
Ser-Gly-His-Gln-Leu-Leu-Leu-Asn-Lys-Met-Pro-Asn-Gly-Gly-Gly-Ser (SEQ ID NO: 8),
Ser-Ser-Thr-Leu-Lys-Thr-Phe-Phe-Gly-Phe-Pro-Asp-Gly-Gly-Gly-Ser (SEQ ID NO: 9),
Asp-Ser-Ser-Asn-Pro-Ile-Phe-Trp-Arg-Pro-Ser-Ser-Gly-Gly-Gly-Ser (SEQ ID NO: 10),
Asn-Thr-Ser-His-Leu-Arg-Val-Lys-Leu-Pro-Thr-Pro-Gly-Gly-Gly-Ser (SEQ ID NO: 11),
Ser-Gly-His-Gln-Leu-Leu-Leu-Asn-Lys-Met-Pro-Asn-Gly-Gly-Gly-Ser (SEQ ID NO: 12),
Ala-Thr-Trp-Ser-His-His-Leu-Ser-Ser-Ala-Gly-Leu-Gly-Gly-Gly-Ser (SEQ ID NO: 13),
Ser-Tyr-Ser-Gln-Met-Asp-Pro-Pro-Arg-Ser-Leu-Pro-Gly-Gly-Gly-Ser (SEQ ID NO: 14),
Thr-Met-Arg-Asn-Pro-Ile-Thr-Ser-Leu-Ile-Ser-Val (SEQ ID NO: 15),
Leu-Leu-Ala-Asp-Thr-Thr-His-His-Arg-Pro-Trp-Thr (SEQ ID NO: 16),
Lys-Glu-Ile-Pro-Pro-Ile-Pro-Leu-Leu-Ala-Pro-Ser (SEQ ID NO: 17),
Asn-Asn-Val-Ser-Gln-Lys-Trp-Gln-Gln-Arg-Leu-Ile (SEQ ID NO: 18),
Asn-Ser-Met-Ile-Ala-His-Asn-Lys-Thr-Arg-Met-His (SEQ ID NO: 19),
Gly-Ile-His-Val-Pro-Trp-Met-Pro-Pro-Val-Ala-Phe (SEQ ID NO: 20),
Gln-Arg-Ser-Trp-Thr-Leu-Asp-Ser-Ala-Leu-Ser-Met (SEQ ID NO: 21),
Ser-Gly-His-Gln-Leu-Leu-Leu-Asn-Lys-Met-Pro-Asn (SEQ ID NO: 22),
Ser-Ser-Thr-Leu-Lys-Thr-Phe-Phe-Gly-Phe-Pro-Asp (SEQ ID NO: 23),
Asp-Ser-Ser-Asn-Pro-Ile-Phe-Trp-Arg-Pro-Ser-Ser (SEQ ID NO: 24),
Asn-Tyr-Ser-His-Leu-Arg-Val-Lys-Leu-Pro-Thr-Pro (SEQ ID NO: 25),
Ser-Gly-His-Gln-Leu-Leu-Leu-Asn-Lys-Met-Pro-Asn (SEQ ID NO: 26),
Ala-Thr-Trp-Ser-His-His-Leu-Ser-Ser-Ala-Gly-Leu (SEQ ID NO: 27), and
Ser-Tyr-Ser-Gln-Met-Asp-Pro-Pro-Arg-Ser-Leu-Pro-Gly-Gly-Gly-Ser (SEQ ID NO: 28).

Ra is (a14) U-Lys(U)-Lys(U)-Gly-OH, and U is one selected from the group consisting of -Lys, -Lys-(Asp-NHAc)$_J$, —NHAc, -Lys-(Asp-)$_k$-NHAc and (Asp-NHAc)$_J$, wherein J is 1 or 2, and K is an integer, 1≤K≤20.

In an appropriate embodiment of the present invention, the term "alkyl group" refers to a saturated linear hydrocarbon group or hydrocarbon group with branch chain(s), and a $C_1$-$C_{10}$ alkyl group refers to a saturated linear hydrocarbon group or hydrocarbon group with branch chain(s) containing 1 to 10 carbon atoms. Therefore, a $C_1$-$C_{10}$ alkyl refers to methyl, ethyl, propyl, butyl, isobutyl, sec-butyl, pentyl, 2-methylbutyl, 3-methylbutyl, hexyl, heptyl, octyl, nonyl or decyl. The "unsaturated alkyl group" refers to a hydrocarbon group being a double bond linear chain, triple bond linear chain or with double bond or triple bond branch chain(s). A "phenylamino group" is expressed by —NHPh to represent that there is a substituted group of amino in the structure of the phenyl group.

In an appropriate embodiment, the manufacture of the dihydroxypentanoate derivatives according to Formula I uses solid-phase peptide synthesis (SPPS) method through standard Fmoc protection strategy and shown in the synthesis pathway of FIG. 1. Gly-preloaded Wang resin is the starting material. It reacts with Fmoc-Lys($^{iv}$Dde)-OH first, and then with simvastatin in dimethylformamide (DMF) to obtain compound 12. Hydrazine is utilized to remove the $^{iv}$Dde protecting group from compound 12, and then couples the free amine with six Fmoc-Asp($^t$Bu)-OH to obtain compound 13. After remove Fmoc, Fmoc-Lys($^{iv}$Dde)-OH) is conjugated with compound 13 to obtain compound 14. Afterward, PEG$_{500}$-NPC (compound 15) is conjugated on compound 14 and then change N-terminal Fmoc with acetyl or fluorescein isothiocyanate (FITC) to obtain compound 1 and 1-F.

Figure 2:
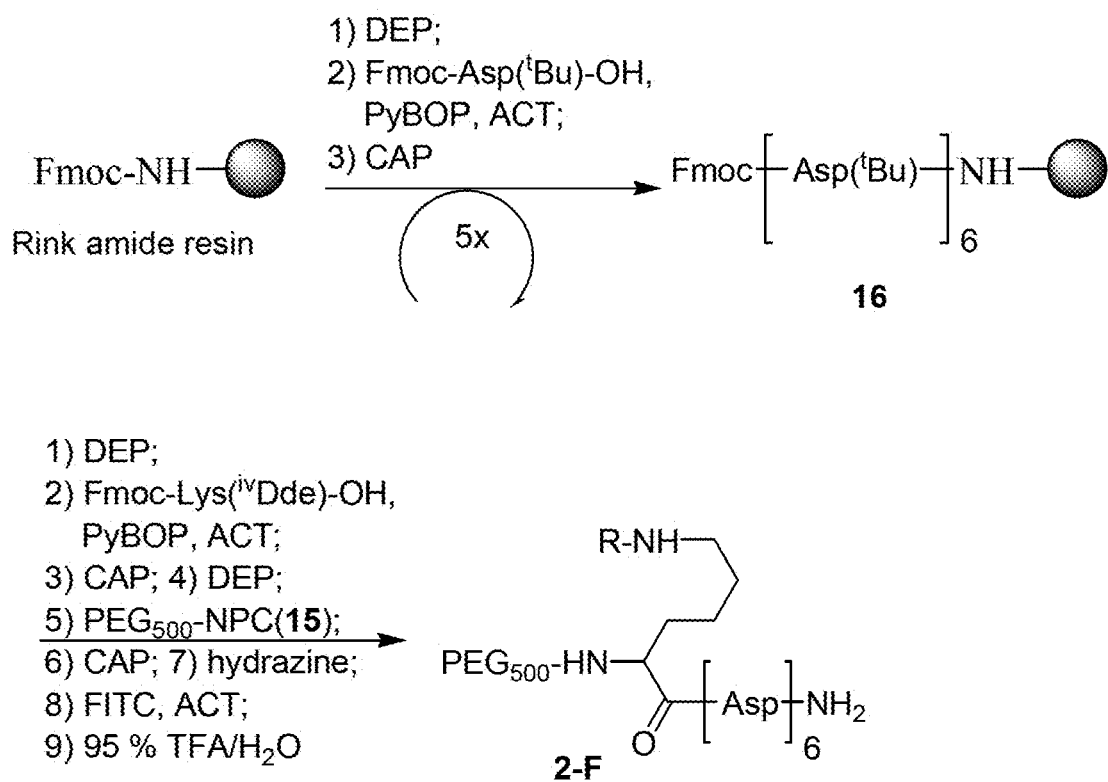
FIG. 2 shows the scheme B of the manufacturing method.

The synthesis pathway of compound 2-F is shown in FIG. 2, Rink amide resin is the starting material, and six Fmoc-Asp($^t$Bu)-OH are conjugated thereonto to obtain compound 16. Afterward, Fmoc-Lys($^{iv}$Dde)-OH), PEG$_{500}$-NPC (compound 15) and fluorescein isothiocyanate (FITC) are installed on compound 16 and then the peptide was cleaved from resin to obtain compound 2-F.

Figure 3:
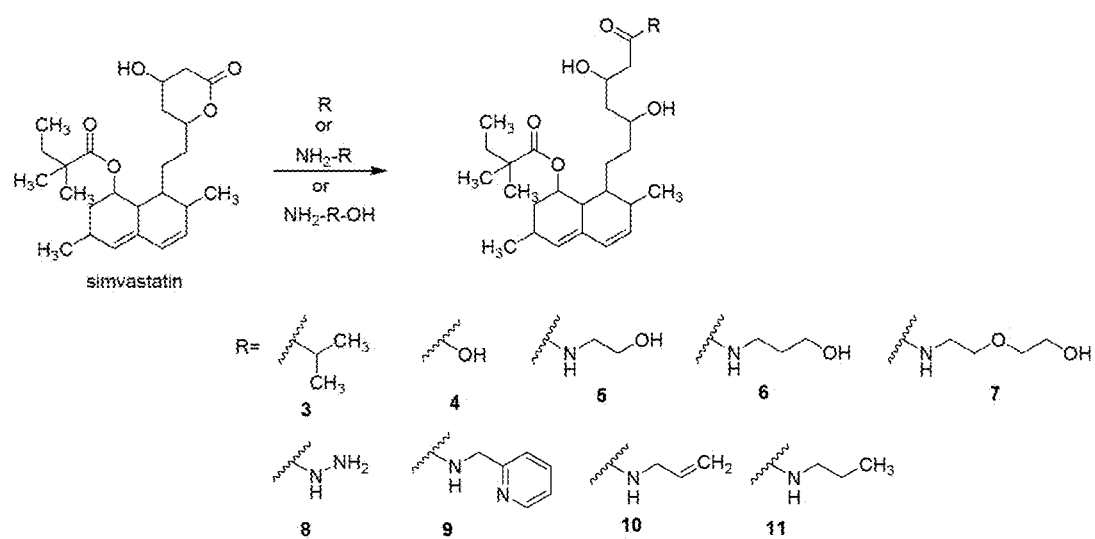
FIG. 3 shows the scheme C of the manufacturing method.

3,5-dihydroxypentanoate derivatives can be synthesized by treating simvastatin with isopropyl Grignard reagent in dried tetrahydrofuran (THF) at room temperature. The synthesis pathway is shown in FIG. 3.

In an appropriate embodiment of simvastatin acid derivatives according to Formula I, Rh is one selected from the group consisting of compounds represented by Formulae (A), (B), (C), (D), (E) and (F). Some of the simvastatin acid derivatives are according to Formula II, and Rt is one selected from the group consisting of a $C_1$-$C_{10}$ alkyl group, a hydroxyl group, a alkylamino group, —NH—($C_1$-$C_{10}$)alkyl-Rz, —NH—($C_1$-$C_5$)alkyl-O—($C_1$-$C_5$)alkyl-Rz, —NH-amino group.

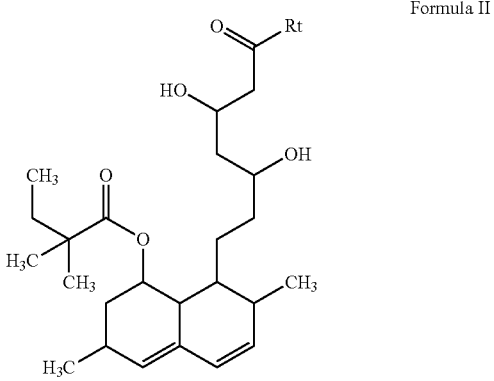

Formula II

Rz is one selected from the group consisting of a $C_1$-$C_{10}$ unsaturated alkyl group, a hydroxyl group, an amino group, furan, a six-member aromatic ring with at least one oxygen atom, pyrrole and pyridine.

The synthesis pathway in FIG. 3 shows the manufactures of the simvastatin acid derivatives according to Formula II. Simvastatin acid (compound 4) and its derivatives compounds 5-9 can be synthesized according to this synthesis pathway, in which simvastatin reacts with various types of amines compounds in dichloromethane, methanol or tetrahydrofuran.

According to the above pathways for the present invention, the synthesis of the peptide derived 3,5-dihydroxypentanoate can use the synthesis pathway shown in FIG. 1 or 2, and the manufacture of nonpeptide 3,5-dihydroxypentanoate derivatives uses the synthesis pathway shown in FIG. 3. In these synthesis pathway, the simvastatin derivatives can be the starting material, which can be selected from commercially available or conventional statins. For example, the chemical name of atorvastatin is (3R,5R)-7-[2-(4-Fluoro-phenyl)-3-phenyl-4-(phenyl-carbamoyl)-5-propan-2-ylpyrrol-1-yl]-3,5-dihydroxy-heptanoic acid), the chemical name of cerivastatin is (3R,5S,6E)-7-[4-(4-fluoro-phenyl)-5-(methoxymethyl)-2,6-bis(propan-2-yl)pyridin-3-yl]-3,5-dihydroxy hept-6-enoic acid), the chemical name of fluvastatin is (3R,5S,6E)-7-[3-(4-Fluorophenyl)-1-(1-methylethyl)-1H-indol-2-yl]-3,5-dihydroxy-6-heptenoic acid), the chemical name of lovastatin is (1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl (2S)-2-methylbutanoate), the chemical name of mevastatin is (1S,7R,8S,8aR)-8-{2-[(2R,4R)-4-hydroxy-6-oxotetrahydro-2H-pyran-2-yl]ethyl}-7-methyl-1,2,3,7,8,8a-hexahydronaphthalen-1-yl (2S)-2-methylbutanoate), the chemical name of pitavastatin is (3R,5S,6E)-7-[2-cyclopropyl-4-(4-fluorophenyl)-3-quinolyl]-3,5-dihydroxy-6-heptenoic acid), the chemical name of pravastatin is (3R,5S,6E)-7-[2-cyclopropyl-4-(4-fluoro-phenyl)quinolin-3-yl]-3,5-dihydroxyhept-6-enoic acid), the chemical name of rosuvastatin is (3R,5S)-7-[4-(4-Fluoro-phenyl)-6-isopropyl-2-(N-methyl-N-methanesulfonyl-amino)pyrimidin-5-yl]-3,5-dihydroxy-6(E)-heptenoic acid), and the chemical name of simvastatin is (1S,3R,7S,8S,8aR)-8-{2-[(2R,4R)-4-hydroxy-6-oxotetrahydro-2H-pyran-2-yl]ethyl}-3,7-dimethyl-1,2,3,7,8,8a-hexahydronaphthalen-1-yl2,2-dimethylbutanoate.

The term "treat" and the derivatives thereof refer to a method for slowing down, improving, reducing or eliminating any symptoms or related symptoms of the disease which the patient has, and a method for preventing the disease and any symptoms related thereto. The term "therapeutically effective amount" refers to a sufficient dosage that can improve or prevent the symptoms of the disease or prevent the condition of the organism from setting worse. The "effective amount" also means that the dosage of the administrated compound is sufficient for use in diagnosis. Unless there is another description in the specification, "active compound" and "pharmaceutically active compound" both can be used interchangeably herein, and they refer to compounds with pharmaceutics, pharmacology or therapeutical effects.

The terms "excipient", "pharmaceutically acceptable carrier or excipient", "bioavailable carrier or excipient", are comprised of a solvent, dispersing agent, coating, antibacterial agent, antifungal agent, preservative, etc. for use in manufacturing the Formulations. Typically such a carrier or expicient itself does not actively treat disease, and the derivatives disclosed in the present invention collocated with various kinds of pharmaceutically acceptable carriers or excipients to prepare various Formulations for administration to animals or humans will not cause a harmful reaction, allergy or other inappropriate reaction. Therefore, the derivatives disclosed in the present invention collocated with various kinds of pharmaceutically acceptable carriers or excipients are suitable for use clinically for use in humans.

The term "pharmaceutically acceptable excipient" includes but be not limited to at least one of a polymer, resin, plasticizer, filler, lubricant, diluent, binding agent, disintegration agent, solvent, surfactant, preservative, sweetener, flavoring agent, pharmaceutical dye or pigment, and viscosity agent.

The term "pharmaceutical composition" is a solid or fluid composition whose form, concentration and purity are suitable for administration to patients such as humans or animals. After administration, the pharmaceutical composition can induce the desired physiological change. The pharmaceutical composition is typically sterile and/or non-pyrogenic.

The carrier can be adjusted according to various Formulations. The composition of the sterile injection can be dissolved or suspended in a nontoxic diluent or solvent for intravenous injection, such as 1,3-butanediol. The acceptable carrier can be mannitol or water. The conventional solvents are fixed oil, synthesized glycerolipid or diglyceride. Fatty acids, such as oleic acid, olive oil or castor oil derivatives and the like, glycerides, especially oxy-acetylated types, can all be manufactured as an injection using a natural pharmaceutically acceptable oil. Such an oil solution or suspension can include a long-chain alcohol diluent or a dispersing agent, carboxymethyl cellulose or similar dispersing agents. Other conventional surfactants such as Tween or Spans, or other similar emulsifier, or pharmaceutically acceptable solid, fluid or other bioavailable enhancement agent can be used during the development of the pharmaceutical Formulations.

Oral administration compositions may adopt any kind of orally acceptable Formulations, which include a capsule, lozenge, tablet, emulsion, aqueous suspension, dispersing agent or solvent. The conventional carriers used in oral Formulations, such as the basic additives of a lozenge, can be lactose, corn starch, lubricant or magnesium stearate. The diluent used in the capsule may include lactose or dried corn starch. To manufacture the aqueous suspension or emulsifying agent forms, the active compounds are suspended or dissolved in an oil surfactant mixed with emulsifying or suspending agents, and sweetener, flavor or pigment is then added if necessary.

The aerosol or inhalation compositions can be manufactured according to conventional manufacturing techniques. For example, the composition is dissolved in normal saline, and benzyl alcohol or another suitable preservative can be added, or enhancing absorbers can be added to improve the bioavailability. The compound disclosed in the present invention can also be manufactured as a suppository, which can be administered to the rectum or vagina.

The compounds disclosed in the present invention can also be administrated by injection, which includes via subcutaneous, intraperitoneal, intravenous, intramuscular, intra-articular, intracranial, intra-articular fluid, intraspinal, aortic, pleural, intra-disorders site injection, or another suitable administration technique.

In an appropriate embodiment, the patient is administrated with the composition including the compound of Formula I which is a combination therapy, and the manufactured single Formulation of the oral composition can be a tablet, capsule or food that includes the compound of Formula I. For the combination therapy administrating different Formulations of the Formula I compound, the administration all at once or over short time intervals can be varied according to the condition and age of the patient. The Formulations can include the oral dosage form of sublingual or buccal tablets, rectal administration, nasal administration, dry powder or a spray inhaler, and even vaginal administration, subcutaneous, intramuscular, intravenous and intradermal injections, topical administration, etc., such as a hand cream, spray, solution, lotion, gel, cream, ointment, paste, unguent, emulsion or suspending agent, can further include oral or injection administration. The short time interval administration is usually finished in 3 hours.

All of the technical and scientific terms described in the present specification, unless otherwise defined, all belong to knowledge that those ordinarily skilled in the art can commonly understand.

The 3,5-dihydroxypentanoate of simvastatin acid is modified using aspartate oligopeptides and polyethylene glycol to obtain compounds 1-F and 1, and compound 1-F is further bonded with a fluorescent group. Comparatively, the structure of compound 2-F does not have simvastatin acid, and only has aspartate oligopeptides, polyethylene glycol and a fluorescent group. In the structures of compounds 1-F and 1, the ring of a lactone group of simvastatin is opened using the amino group of aspartate oligopeptides and binds to the carboxyl group of 3,5-dihydroxypentanoate via an amide bond formation.

In compounds 1-F and 1, the ring of the lactone group of simvastatin can be opened and modified using non-oligopeptide with an amino group via an amide bond formation, and even using the compounds without an amino group to form the keto form to prepare simvastatin derivatives 3-11.

The inhibitory activities of simvastatin acid (compound 4) and the derivatives 1-F and 5-11 to HMG-CoA reductase were tested, and the results are shown in Table 1. All of the effective inhibitory concentrations of simvastatin derivatives were higher than that of simvastatin itself, and even the effective inhibitory concentrations of compounds 1-F and 9 are 500-fold higher than that of simvastatin. Therefore, it can be seen that when the ring of the lactone group of simvastatin is opened and forms an amide bond, it can effectively reduce the inhibitory activity of HMG-CoA reductase.

TABLE 1

| Compound | $IC_{50}$ (nM) |
|---|---|
| Simvastatin | 56.1 ± 2.1 |
| Compound 1-F | >30000 |
| Compound 4 | 263.2 ± 83.4 |
| Compound 5 | 1024.5 ± 50.9 |
| Compound 6 | 1127.9 ± 89.5 |
| Compound 7 | 171.2 ± 9.2 |
| Compound 8 | 950 ± 80.1 |
| Compound 9 | >30000 |
| Compound 10 | 26620 ± 620.2 |
| Compound 11 | 21560 ± 330.2 |

Figure 4:
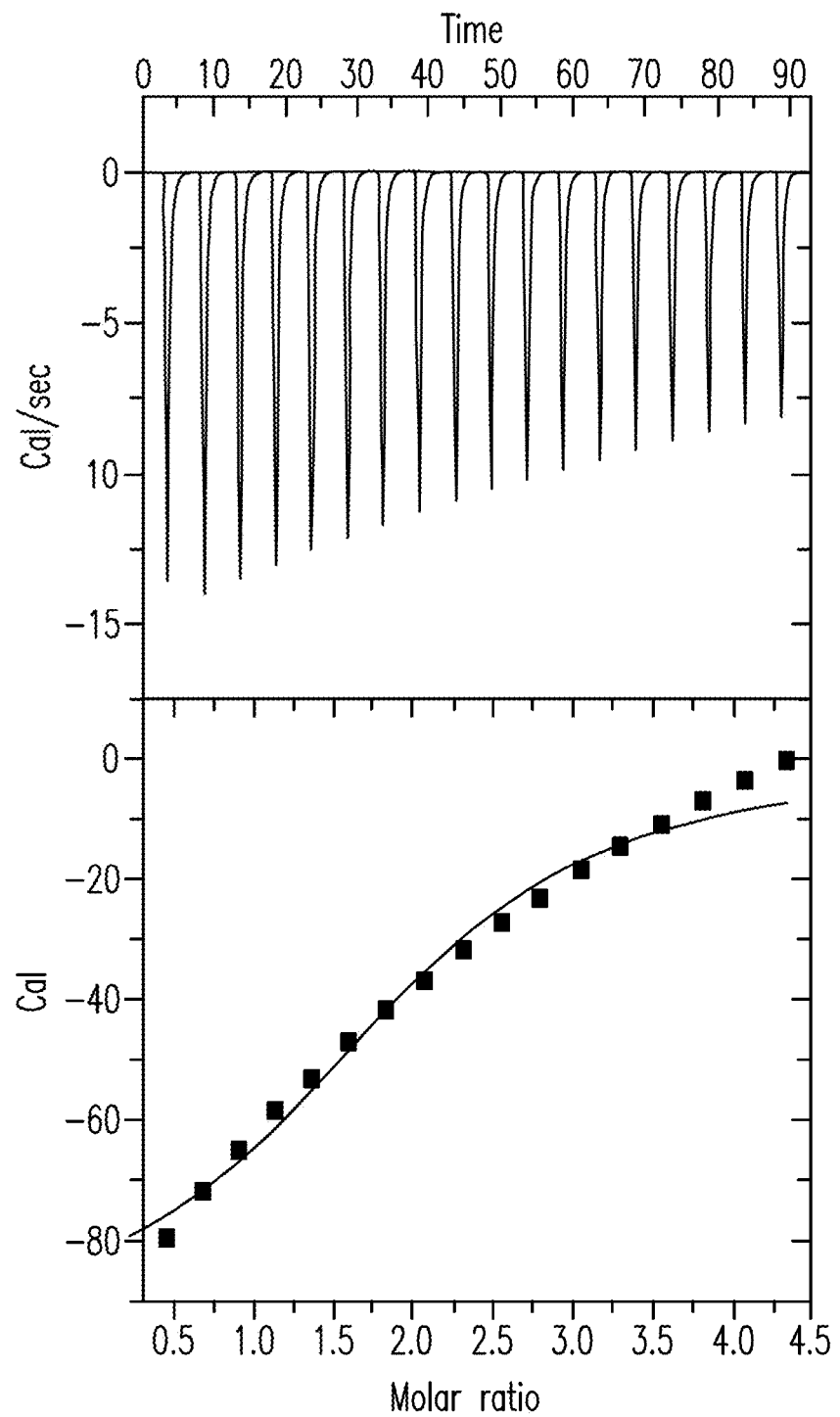
FIG. 4 shows the isothermal titration calorimetry (ITC) binding curves of compound 1 in combination with calcium ions.

The binding affinity of compound 1 to calcium ions was measured using isothermal titration calorimetry (ITC), and the results are shown in FIG. 4. Compound 1 can bind with up to two calcium ions with strong binding affinity, and the binding constant is 278.1 $kM^{-1}$.

Figure 5:
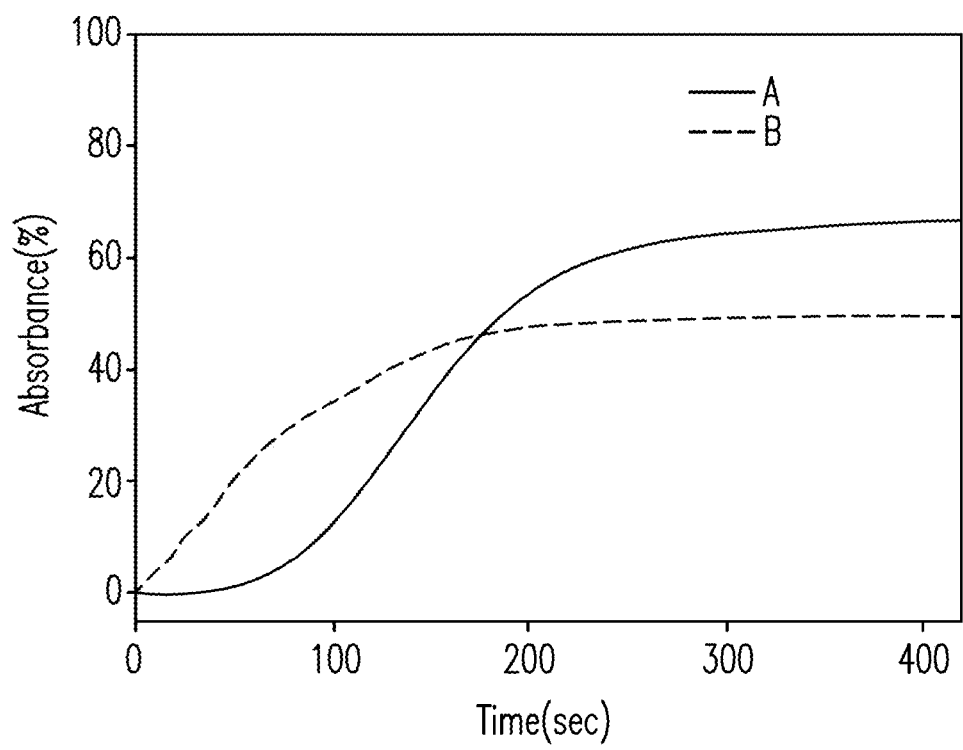
FIG. 5 shows that compound 1 affects the sedimentation of hydroxyl apatite for (A) compound 1+hydroxyl apatite and (B) hydroxyl apatite.

Hydroxyapatite (HAP) is an inorganic composition of bone, HAP was common used as the bionic bone material in the research. The results of the affinity test of compound 1 for HAP are shown in FIG. 5. The delayed segmentation of HAP in the presence or absence of compound 1 is represented by the percentage of light transmittance (% T). Compared with the group without the addition of compound 1, it can be seen that the segmentation of HAP was delayed up to 120 seconds because of compound 1 existence.

Figure 6A:
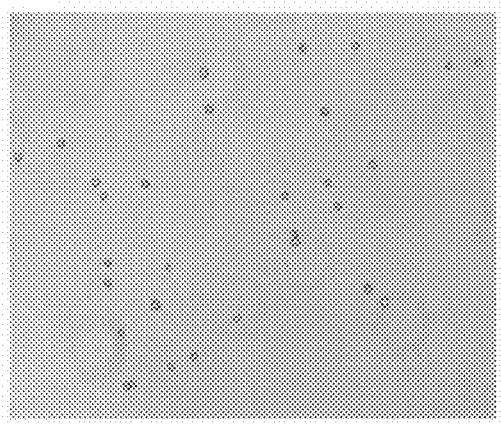
FIGS. 6(a) and 6(b) show that compound 1-F combines with hydroxyl apatite in (a) bright field and (b) fluorescence field.
Figure 6B:
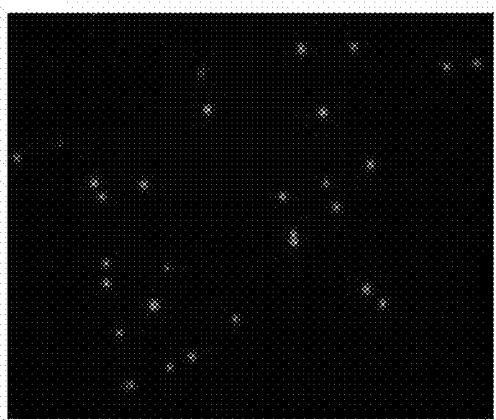

If compound 1-F is combined with HAP, it can be monitored using a fluorescent microscope. The results are shown in FIG. 6. Compound 1-F combines on the surface of HAP so that the HAP particles represent fluorescence.

Statins are known agents that induced stem cells to be osteogenesis. Human adipose derived stem cells (hADSC) were used as the test material to evaluate the toxicities of peptide modified simvastatin. It was discovered that the cell viability was refer to cell proliferation after treated with compound 1-F was much higher than that cells treated with simvastatin. Expressed in terms of $IC_{50}$, it can be seen that $IC_{50}$ of compound 1-F is 300-fold of that of simvastatin, and it is obvious that the cell safety of compound 1-F is much higher than that of simvastatin. (Table 2)

TABLE 2 the cytotoxicity test of the compounds on human adipose stem cells

| Compound | $IC_{50}$ (µM) |
|---|---|
| Simvastatin | 3.25 ± 0.31 |
| Compound 1-F | >1000 |

Before induced the cell osteogenesis, rat bone marrow stem cells, D1 cells, were used as the test material to evaluate the cytotoxicities of the simvastatin derivatives. D1 cell is more sensitive than hADSC cell by drug treatment. The results are shown in Table 3. All of the concentrations of simvastatin derivatives are higher which indicates that the safety of the simvastatin derivatives for the D1 cells was higher than that of simvastatin. Notably, $IC_{50}$ of compound 7 is 83-fold higher than that of simvastatin.

TABLE 3

| Compound | $IC_{50}$ (µM) |
|---|---|
| Simivastin | 3.25 ± 0.31 |
| Simivastin acid (4) | 29.40 ± 1.02 |
| 5 | 117.00 ± 8.07 |

TABLE 3-continued

| Compound | IC$_{50}$ (µM) |
| --- | --- |
| 6 | 161.08 ± 3.76 |
| 7 | 269.13 ± 1.04 |
| 8 | 105.7 ± 3.3 |
| 9 | 97.3 ± 7.9 |
| 10 | 92.2 ± 2.1 |
| 11 | 94.1 ± 10.6 |

Figure 7:
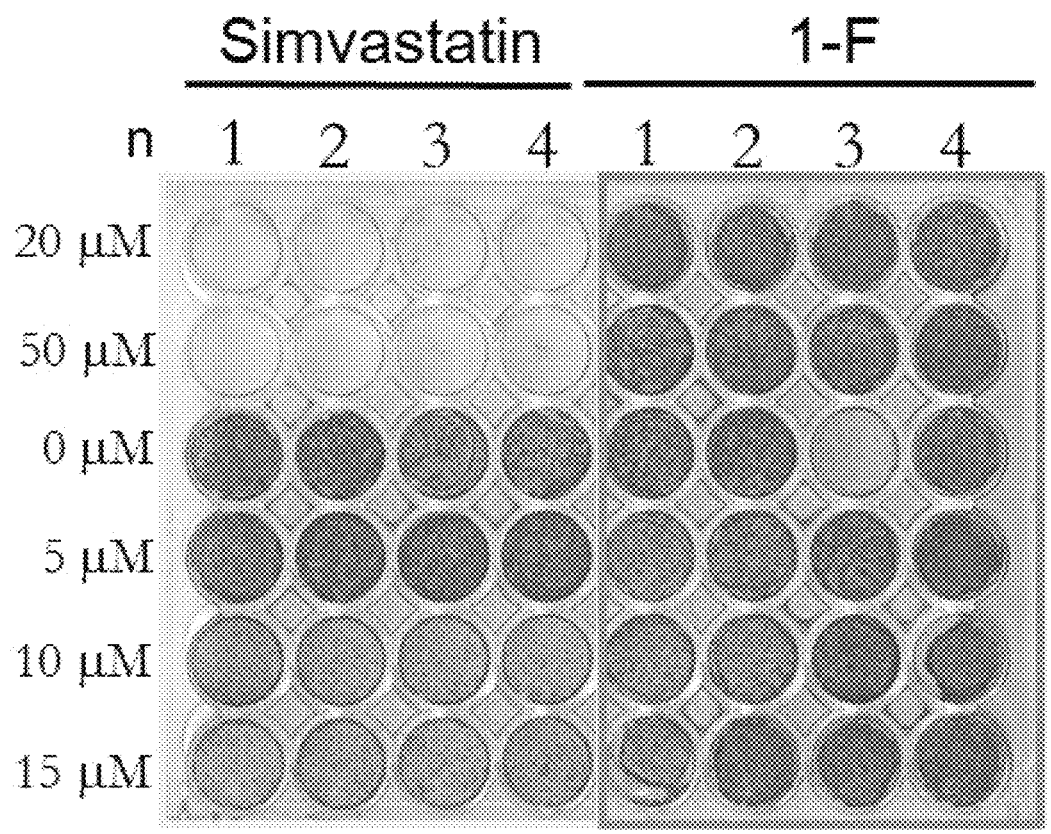
FIG. 7 shows the induction of mineralization of simvastatin and compound 1-F to human adipose-derived stem cells.

Following the tests above, the ability of inducing mineralization of the compounds to D1 cells was tested. The results are shown in FIG. 7. Simvastatin and compound 1-F both can induce mineralization of D1 cells under a concentration of 15 µM. However, simvastatin causes cytotoxicity resulting in cell death and becomes more severe with an increased concentration of simvastatin. Thus the degree of mineralization is reduced, which can be seen from the weakened red dye in the simvastatin group in FIG. 7. By comparison, compound 1-F can steadily induce cell mineralization. When the concentration is raised to over 20 µM, only compound 1-F can induce mineralization of D1 cells, and all the cells in the simvastatin group died. Summing up the analysis of cytotoxicity and mineralization, compared with simvastatin, compound 1-F can induce cell mineralization safely and effectively.

Figure 8A:
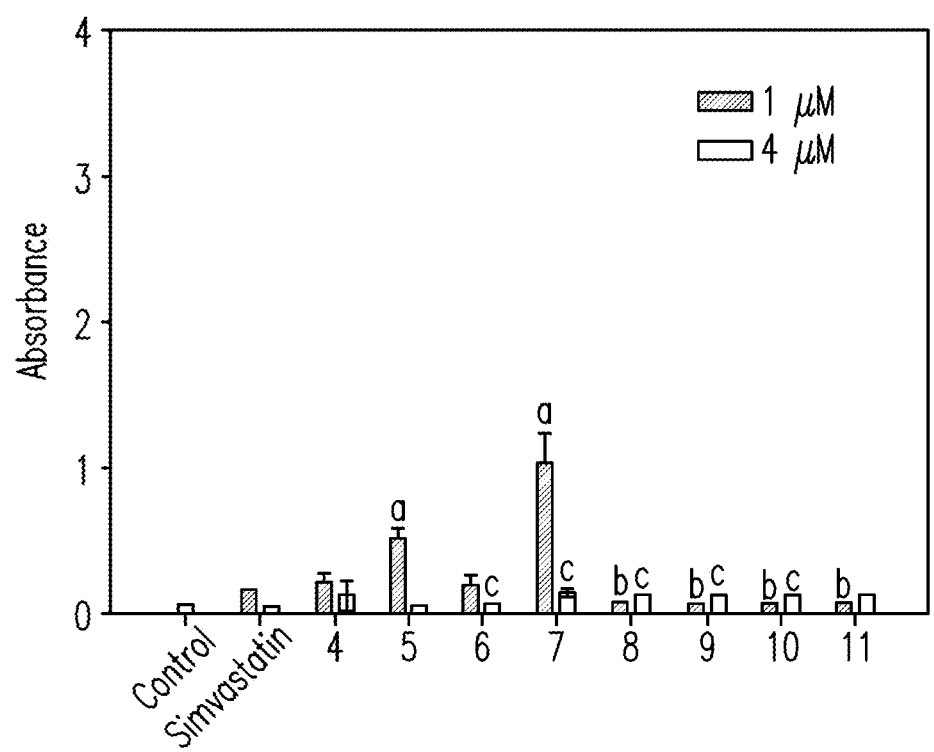
FIGS. 8(a) to 8(c) show the result of induction mineralization of simvastatin and compounds 4~11 to D1 cells.
Figure 8B:
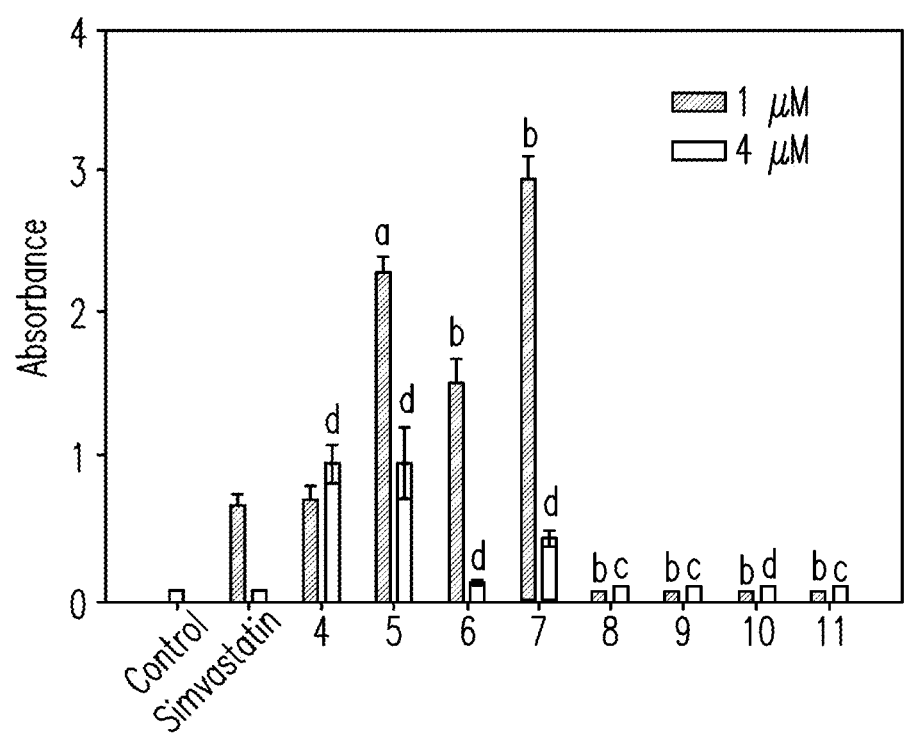
Figure 8C:
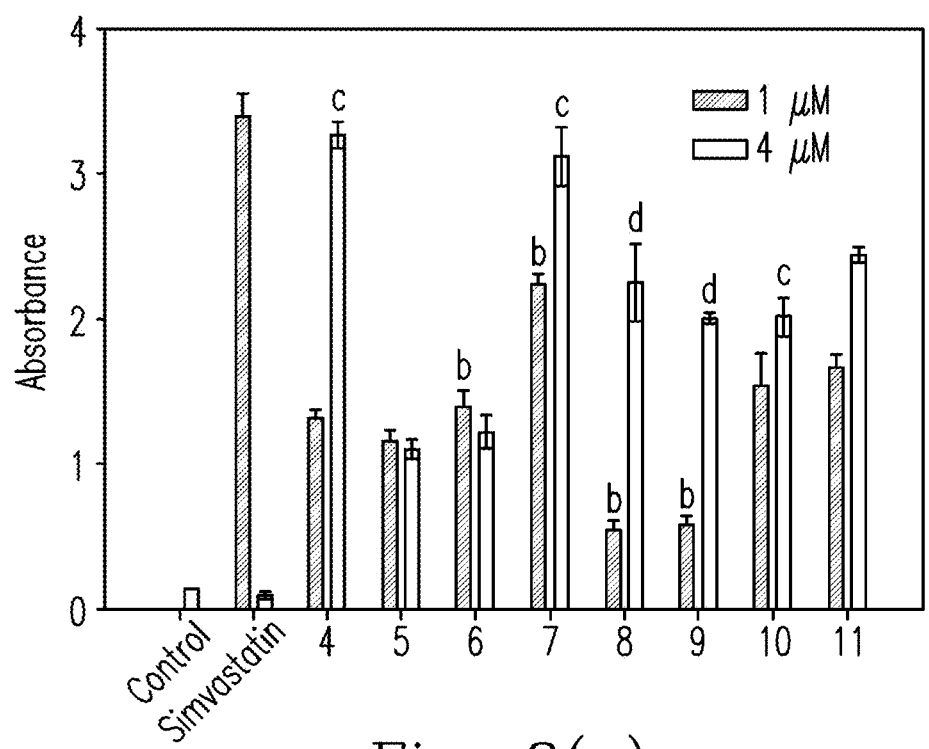

For non-peptide modified derivatives, the inducing mineralizations of D1 cells were evaluated and the concentrations of simvastatin acid (compound 4) and compounds 5~11 were fixed at 1 µM and 4 µM. As shown in FIG. 8(a), compounds 5 and 7 (1 µM) clearly induced cell mineralization by Day 9. As shown in FIG. 8(b), compounds 5, 6 and 7 (1 µM) all have excellent ability to induce cell mineralization by Day 11, especially compound 7. As shown in FIG. 8(c), all the compounds have the ability to induce cell mineralization. When simvastatin at 1 µM has excellent inducing ability, however, more than 1 µM of simvastatin causes D1 cell death. By comparison, simvastatin acid (compound 4) can only induce mineralization effectively under a concentration of 4 µM. We conclude that the difference results from the abilities of these two compounds entering cells. Compound 7, whose solubility is higher than simvastatin, has the obvious ability to induce cell mineralization under a concentration of 4 µM, equivalent to simvastatin (1 µM) and simvastatin acid (4 µM).

Figure 9A:
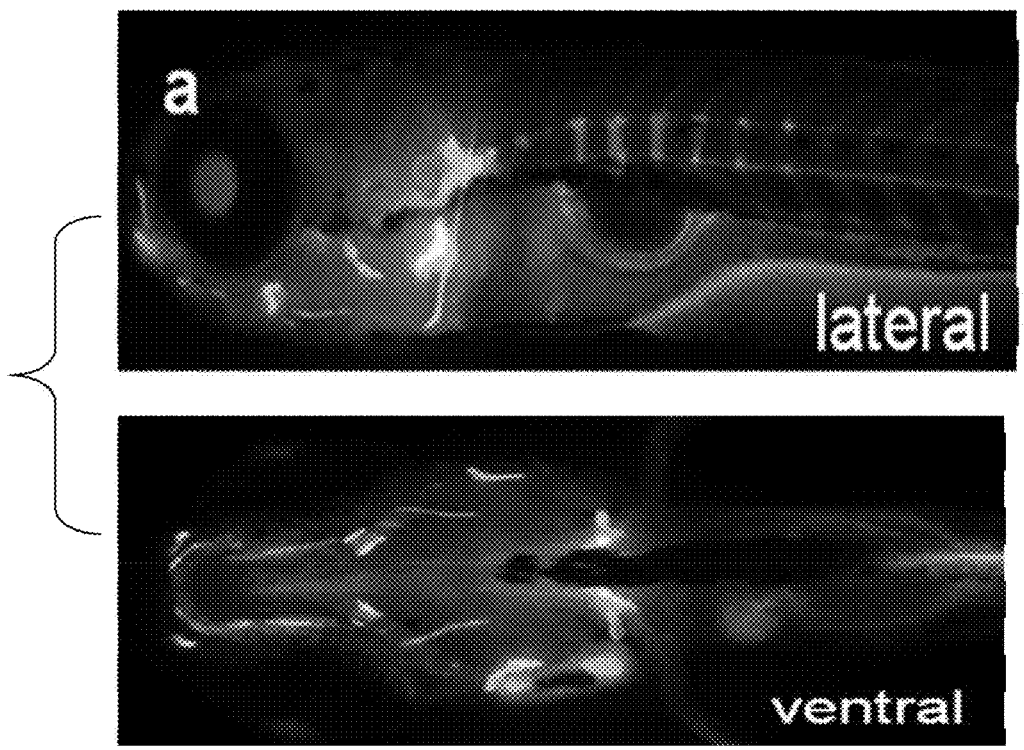
FIGS. 9(a) to 9(c) show bone-targeting (a, b) and promotion of bone formation (c) effects on a zebra fish by monitoring the dark field under fluorescent microscope detection, wherein (a) after feeding calcein to the zebra fish; (b) after feeding compound 2-F to zebra fish; and (c) after feeding compounds 1-F, 2-F and simvastatin to zebra fishes, the bone density of the zebra fishes were measure.
Figure 9B:
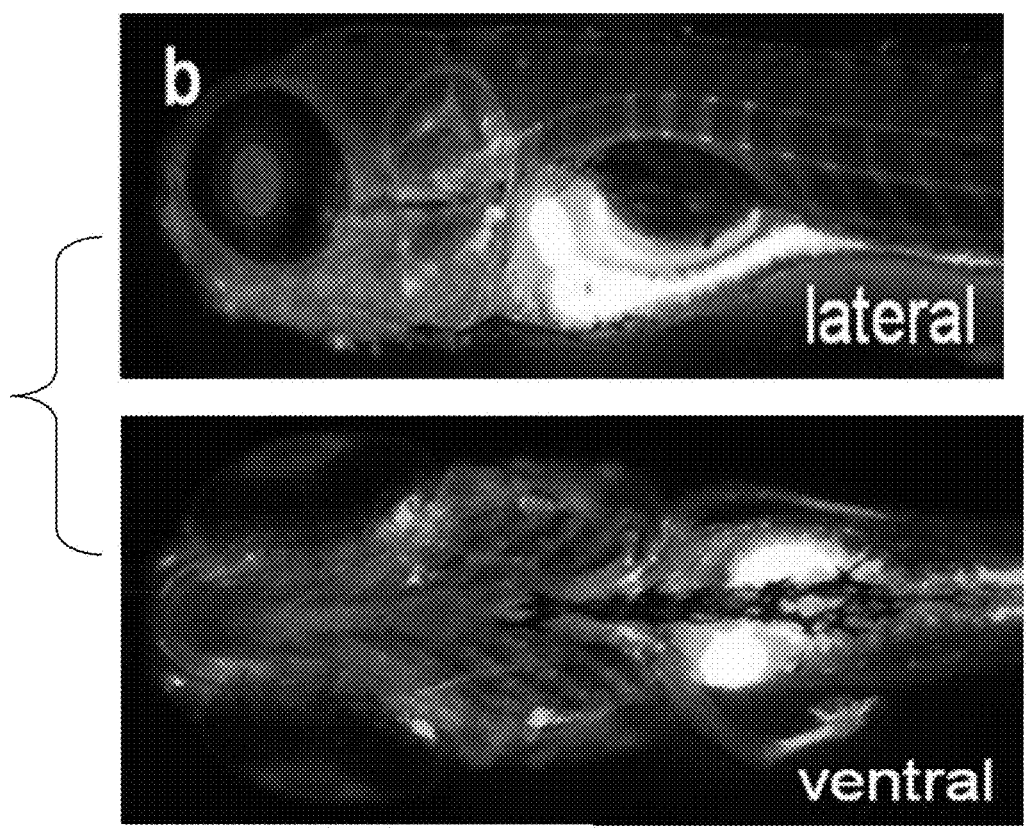
Figure 9C:
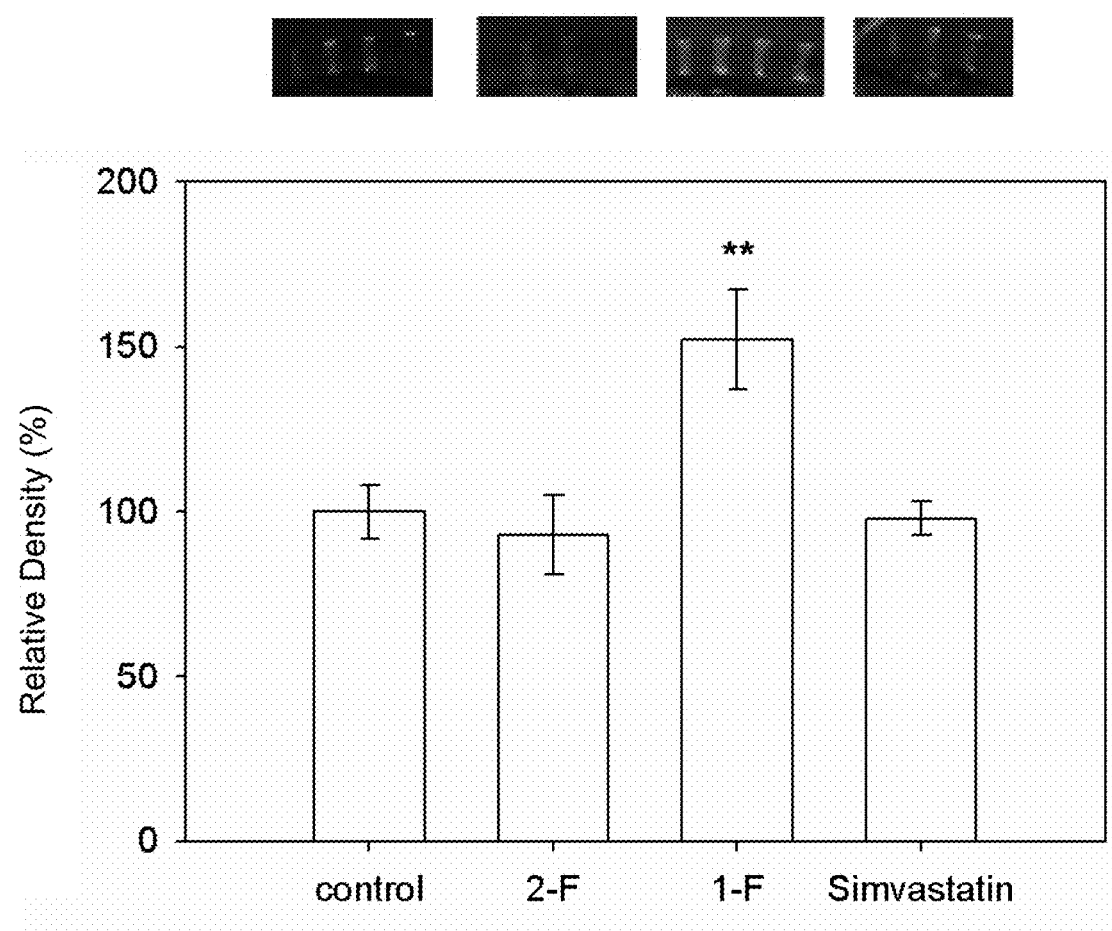
Figure 10:
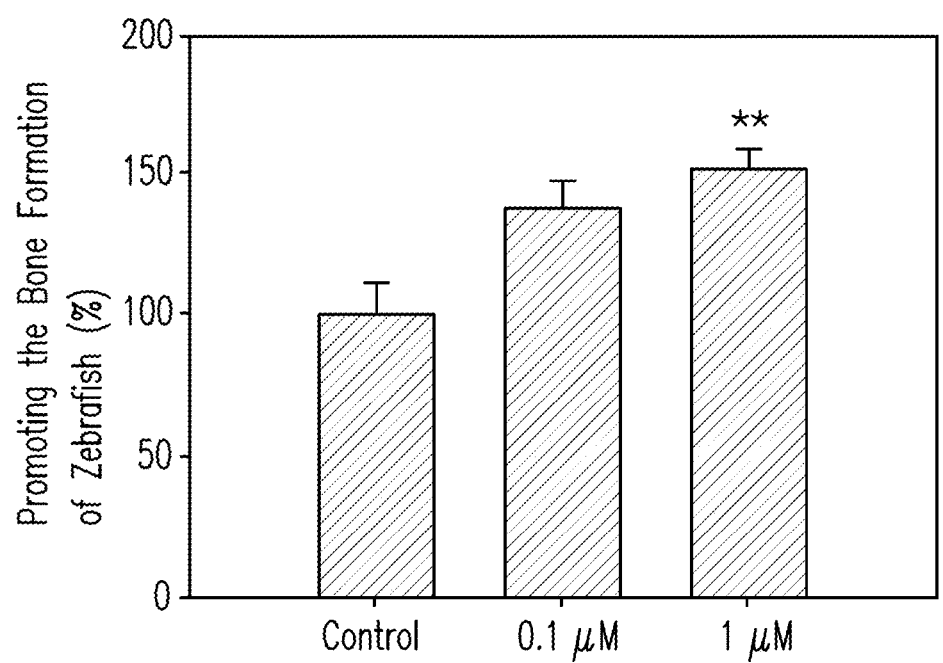
FIG. 10 shows the results that compound 7 promoted bone formation in the zebra fish.

The Fleming team reported that the gene type, physiological characteristics and growth patterns of bones in zebrafish are similar to those of humans, and these similarities between humans and zebrafish are greater than those between humans and mice, and thus zebrafish are suitable as a screening platform for developing bone-related drugs. The bone formation of derivative compounds 1-F, 2-F, 7 and simvastatin were evaluated, and the bone-targeting ability of compound 2-F was further analyzed in living zebrafish. (FIGS. 9 and 10)

Calcein, which is a known staining dye for the mineral in animals, was used as a positive control group. After feeding the zebrafish with calcein, the fluorescent staining on the bone can be observed using a fluorescence microscope (the lateral and front observations of the zebrafish are shown in FIG. 9(a)). As shown in FIG. 9(b), the fluorescence stained on the bones after compound 2-F feeding to the zebrafish, it proves that compound 2-F can be targeted to the bones.

Testing the effect of the compounds on the bone formation of the growing zebrafish was achieved by administering compounds 1-F, 2-F and simvastatin to the zebrafish. It was discovered that compound 1-F promoted bone formation of up to 50% compared with the non-administration group (control), and simvastatin and compound 2-F did not promote bone formation as shown in FIG. 9(c). Compared to the structures of compounds 1-F and 2-F, it concluded that the existence of 3,5-dihydroxypentanoate contributed the bone formation of compound 1-F. Furthermore, Fleming, responding to the statement that simvastatin has different effects on human bones, reported that simvastatin does not benefit in the bone growth of zebrafish, and the same result was observed in the present invention. Herein, it was proven that compound 1-F with bone-targeting peptides not only targets the bones successfully, but also has excellent potential to promote bone formation in humans.

The non-oligopeptide derivative 7 which had the most outstanding overall performance was selected from the above experiments. In the study for increasing the bone mass of zebrafish, when 0.1 or 1 µM of compound 7 were treated, both can promote bone formation in the zebrafish, and the increase range was between 30% and 50% compared with the non-administration group. As shown in FIG. 10, although compound 7 without the bone-targeting carrier still promoted bone formation, it is obvious that the amide derivative of 3,5-dihydroxypentanoate indeed achieves the effect of bone formation, especially for developing skeleton.

The results show that amide-modified 3,5-dihydroxypentanoate enhances the selectivity of drugs to bone and improves bone formation, and also has the effect of relieving toxicity. These derivatives improve bone formation of statins in zebrafish, and specifically represent the potential of 3,5-dihydroxypentanoate amide derivatives for bone formation for humans in the future. The derivatives of 3,5-dihydroxypentanoate can be a novel bone anabolic agent used to treat low bone mineral density diseases in humans. Compared with inhibiting HMG-CoA reductase using simvastatin, the 3,5-dihydroxypentanoate derivatives affecting the bone mass pathway is independent to the MVA pathway. The present invention first addresses the chemical structure of 3,5-dihydroxypentanoate for bone formation, and explores the inhibition of HMG-CoA reductase is not critical.

Materials and Methods

Cytotoxicity Assay

The cytotoxicity of compound 1-F was analyzed using MTS (3-(4,5-dimethyl-thiazol-2-yl)-5-(3-carboxymethoxyphenyl)-2-(4-sulfophenyl)-2H-tetrazolium) assay. In a 96-well plate, human adipose stem cells (hADSC) were cultured to an initial culture density of $6\times10^3$ cells per well in K medium (Keratinocyte-SFM, GIBCO-Invitrogen Corporation). After the cells filled the wells, the K medium with compound 1-F was set as the experimental group, the K medium without compound 1-F was set as the blank test group, and all were cultured at 37° C. for 3 days. The MTS agent was added to the culture medium for 3 hours, then the medium was removed and the cells were washed with PBS (phosphate buffered saline), and 100 µL of DMSO (dimethyl sulfoxide) was added to the wells to promote the dissolution of formazan. The DMSO solution containing formazan was measured using UV spectrophotometer at 490 nm wavelength, and the survival of cells was judged by the value of absorbance.

The cytotoxicity of compounds 4~11 was analyzed using MTT assay. D1 cells were cultured to an initial culture density of $5\times10^3$ cells per well in a bone medium. The bone medium was a DMEM medium containing 10% Fetal bovine serum (FBS), 100 U/mL penicillin, 100 µg/mL streptomycin, 100 mg/mL ascorbic acid, 1% non-essential amino acids (NEAA) and 1.5 g sodium bicarbonate. After the cells were seeded, the bone medium with compounds 4~11 respectively was set as the experimental group, the bone medium without compound was set as the blank test group, and all were cultured at 37° C. for 3 days. The MTT agent was added to the culture medium for 3 hours, then the medium was removed and the cells were washed with PBS, and 100 μL of DMSO was added to the wells to promote the dissolution of formazan. The DMSO solution containing formazan was measured using UV spectrophotometer at 595 nm wavelength, and the survival of cells was judged by the value of absorbance.

HMG-CoA Reductase Inhibition

A 0.1 M phosphate buffer containing 100 μM HMG-CoA reductase, 330 μM NADPH, 2% DMSO and 1 mg/mL BSA was firstly prepared. Compounds 1 and 4~11 were added dissolved in phosphate buffer at various concentrations, then added HMG-CoA reductase (the final concentration is 17.4 nM) and mixed for 5 minutes. The absorbance of the solution was measured at 340 nm. The $IC_{50}$ values were analyzed via nonlinear least-squares using Sigma 10 to determine the HMG-CoA reductase inhibition of compounds.

Procedures for Culturing and Osteoinduction of D1 Cells

The D1 cells, purchased from American Type Culture Collection, were plated in 48-well plates at a density of $3 \times 10^4$ cells/well. Once confluence was obtained, the cells were cultured in bone medium (BM, prepared with DMEM, 10% FBS, 100 U/mL penicillin, 100 μg/mL streptomycin, 100 mg/mL ascorbic acid, 1% NEAA, 1.5 g sodium bicarbonate) in the presence of compound 1. After 3 days, BM was replaced with an osteogenesis induction medium (OIM prepared with BM, $10^{-2}$ M β-glycerophosphate and $10^{-7}$ M dexamethasone). For all of them, the control had an absence of compound 1. The medium was changed every 2 days. For the quantitative value of mineralization, the cells were washed with PBS triplex and fixed with 10% formalin for 30 minutes at room temperature. Thereafter, the cells were washed with deionized water triplex, and then stained with Alizarin Red S solution (200 mL/well, 80 mM, pH 4) for 10 minutes at room temperature. The cells were washed with deionized water triplex and dried overnight at room temperature. The Alizarin Red S was released from the cell matrix by being mixed with 10% acetic acid$_{(aq)}$ for 30 minutes. The concentration of Alizarin Red S was determined by measuring the absorbance at 415 nm. The difference between the values of blank and experimental groups represents the mineralization abilities of the test compounds induced.

The abilities of compounds 4~11 to induce cell mineralization were evaluated followed the same method above, only remove dexamethasone from the recipe of osteogenesis induction medium.

Bone-Targeting of the Test Compounds

The AB strain of wild-type zebrafish was used for this study. Embryos were collected after natural spawning, staged according to standard criteria, and raised synchronously at 28.5° C. in Hank's buffer (13.7 mM NaCl, 540 M KCl, 25 μM $Na_2HPO_4$, 44 μM $KH_2PO_4$, 300 μM $CaCl_2$, 100 μM $MgSO_4$, 420 μM $NaHCO_3$, pH 7.4). Zebrafish larvae at 2 dpf were exposed to test compounds (3.2 μM) for 3 days in a 24-well plate. At 7 dpf, the fish were anesthetized using tricaine-methanesulfonate (MS 222) and mounted on depression glass slides with methyl-cellulose (3%), and the images of the zebrafish were acquired using a Leica DM-6000 CS fluorescence microscope (Leica Instruments Inc., Wetzlar, Germany). All of the images were acquired using a SPOT Xplorer Digital camera (Diagnostic Instruments, Inc., Sterling Heights, Mich., USA). Each image was taken at 60-sec.

Bone Formation Induced by Test Compounds

Zebrafish larvae at 2 dpf were treated with test compounds (0.32 μM) for 6 days in a 24-well plate. At 7 dpf, the fish were transferred to 6-cm dishes (8 fish/dish) for bone staining using calcein solution. The calcein solution was prepared at 0.2% by dissolving 2 g of calcein powder (Sigma Chemical, St. Louis, Mo.) in 1 liter of deionized water. The immersion time was 10 minutes at 7 dpf. After the immersion, the embryos were rinsed a number of times in fresh water, and then allowed to stand for 10 mins to allow the excess stain diffusion from the larvae tissue. The embryos were then euthanized in tricaine-methanesulfonate (MS 222) and mounted on depression glass slides with methyl-cellulose (3%). The images were acquired using a Leica Z16 APO microscope (Leica Instruments Inc., Wetzlar, Germany) combined with a SPOT Idea digital camera system (Diagnostic Instruments, Inc., Sterling Heights, Mich., USA). Each image was taken at 200 mini-seconds, then the fluorescence of the calcein stain images was calculated using NIH Image J (NIH open software with Macbiophotonics plugins). The outline of individual zebrafish was done using the freehand tool to create ROI. The data was represented as the percentage of relative density of the control group for each treatment.

Statistical Analysis

The experimental results are represented as mean values plus or minus a standard error (MEAN±SEM). Statistical variations between the unpaired and paired samples used a non-dependent Student's t-test. When more than one treatment group was compared with the control group, one-way analysis of variance (ANOVA) or two way repeated measures ANOVA was used. When ANOVA showed significant differences in statistics, a Dunnett's or Student-Newman-Keuls test was used. A P value less than 0.05 indicates that the experimental values had significant statistical differences. Analyzing the information and drawings was performed using SigmaPlot (version 8.0, Chicago, Ill., USA) and SigmaStat (version 2.03, Chicago, Ill., USA).

The present invention is illustrated by the following embodiments, but the present invention is not limited thereby. The drugs and biomaterials used in the present invention are readily available commercially, and the following embodiments only show one of the possible available methods.

General Procedure of Solid Phase Peptide Synthesis (SPPS)

Peptides were synthesized using standard Fmoc-strategy with a Solid Phase Peptide Synthesizer. Generally, Fmoc-Glycine preloaded Wang resin (0.79 mmol/g load) was weighed into the reaction vessel and swelled with freshly DMF (5 mL) for 1 hr prior to synthetic process. Amino acids and PyBOP were used in two-fold excess; the sequential Fmoc groups were removed with 20% piperidine in 5 mL DMF, as "DEP" solution, for 5 min twice, and C terminal of amino acid were activated with 0.4 M N-methylmorpholine in 3 mL DMF, as "ACT" solution, and $Ac_2O$ (100 ••L) was introduced to cap the rest of unreacted free amine, as "CAP" solution. The reactions were monitored by Kaisar test. To add one drop of each solution (0.28 M ninhydrin/ethanol, 42.37 M phenol/ethanol, and pyridine) into resin, the mixture was heated to 120° C. for four minutes (Novabiochem protocol). The sample with free primary amine is indicated by blue resin or solution, but otherwise the resin is achromatic or yellowish situation. Finally, compounds were removed form the solid support by treat with 95% TFA/H$_2$O at room temperature for 1.5 hours.

Embodiment 1: preparing compound 1-F Fmoc-Lys (ivDde)-H was attached to the resin (0.25 g, 0.2 mmol) after reacted for 4 hrs. After the product was exposed in "DEP" to remove Fmoc group, the solution of simvastatin (0.4 mmol, 0.16 g) in 10% diisopropylethylamine/DMF was subjected into the vessel and reacted with resin under 200 W of radiation at 105° C. for 1.5 hr by assisted with microwave. Later, to remove ivDde group by using 4% hydrazine, the following six aspartic acids conjugation were carried out by typical condition using Fmoc-Asp(tBu)-H but the reaction times were 30, 45, 60, 80, 80 and 90 min, individually. After that, one more Fmoc-Lys(ivDde)-H was coupled under a 2-hr reaction to conjugate with polyethylene glycol and FITC. After removed Fmoc group, activated polyethylene glycol derivative (0.4 mmol, 0.21 g) was loaded and reacted for 2 hrs. After remove ivDde, the N terminus was modified with FITC (0.4 mmol, 0.15 g) for 60 min or caped with Ac$_2$O, then the peptides were cleaved from resin to obtain compound 1-F.

Embodiment 2: Preparing Compound 1

Following the same steps of the embodiment for preparing compound 1 to obtain compound 14, then polyethylene glycol was conjugated on compound 14 after 2-hour reaction, then the product was acetylated, and then compound 1 was obtained through the CLE steps.

Embodiment 3: Preparing Compound 2-F

After removing the Fmoc, six aspartates were synthesized into 0.251 g (0.2 mmol) of resin sequentially and the reaction time was 30, 45, 60, 80, 80 and 90 minutes to obtain compound 16. A lysine was synthesized into compound 16 for 4 hours, then the compound was modified with polyethylene glycol and FITC for 2 hours and 1 hour respectively, and then compound 2-F was obtained through the CLE steps.

Embodiment 4: Purifying Compound 1

The crude extract was subjected to chromatography in the C18 column, eluted using CH$_3$OH/H$_2$O (7/3) including 0.10% TFA, to generate the desired product (0.110 g), a white powder. Yield was 25%, and R$_f$=0.4 (CH$_3$OH:H$_2$O=7:3). The purity was identified as 95% using C18 column in the HPLC system and analyzed with 220 nm UV detection, using a flow rate of 0.2 mL/min and an isocratic solvent system of 0.1% TFA/CH$_3$OH, for compound 1 (retention time: 7.0 min).

$^1$H-NMR (400 MHz, D$_2$O): δ 5.32 (m, 5H), 4.15 (m, 8H), 4.02 (br, 2H), 3.61 (m, 44H), 3.32 (s, 3H), 3.10 (m, 4H), 2.83 (m, 12H), 1.91 (s, 3H), 1.68 (m, 10H), 1.46 (br, 12H), 1.35 (br, 12H), 1.19 (m, 10H).

Mass (MALDI-TOF): found for 2024 Da (M+H$^+$); calcd. for C$_{89}$H$_{145}$N$_{11}$O$_{41}$: 2023.96 Da.

Embodiment 5: Purifying Compound 1-F

After cleaving the compounds from resin, the filtrates were concentrated in vacuum to produce yellow oil. The crude extract materials were subjected to the LH20 column and eluted by CH$_3$OH to give the desired product of compound 1 (0.122 g, 24%, R$_f$=0.1 in CH$_3$OH/H$_2$O=1/1). The purity was identified as 95% by HPLC with the C18 column with UV detection at wavelength 220 nm and 496 nm, using an isocratic solvent system (0.1% TFA/CH$_3$OH, flow rate: 0.4 mL/min, retention time: 8.2 min).

$^1$H-NMR (400 MHz, acetone-d$_6$): δ 8.50 (br, 1H), 7.92 (m, 1H), 7.16 (m, 3H), 6.71 (m, 11H), 4.74 (m, 6H), 4.30 (s, 2H), 4.13 (m, 6H), 3.58 (m, 44H), 3.30 (m, 3H), 2.89 (m, 12H), 1.84 (m, 16H), 1.53 (br, 8H), 1.27 (m, 18H), 0.88 (m, 2H).

Mass (MALDI-TOF): found for 2469 Da (M+H$_2$O+NaCl+Na$^+$); calcd. for C$_{108}$H$_{154}$N$_{12}$O$_{45}$S: 2369.00.

Embodiment 6: Purifying Compound 2-F

The crude extract was subjected to chromatography in the LH20 column, eluted by H$_2$O, to produce the yellow powder of the desired product (0.091 g). Yield: 26%. R$_f$=0.6 (CH$_3$CN:H$_2$O=1:1). The purity was identified as 95% by the C18 column by HPLC and performed with 220 nm UV detection, using a flow rate of 0.4 mL/min using an isocratic solvent system of 0.1% TFA/H$_2$O, for compound 2-F (retention time: 6.4 min).

$^1$H-NMR (400 MHz, D$_2$O): δ 7.63 (br, 1H), 7.53 (m, 1H), 7.23 (m, 2H), 7.04 (m, 2H), 6.47 (m, 5H), 4.46 (m, 5H), 4.05 (m, 2H), 3.88 (m, 2H), 3.53 (m, 44H), 3.25 (s, 3H), 2.56 (m, 12H), 1.61 (m, 2H), 1.05 (m, 4H).

Mass (MALDI-TOF): found for 1765 Da (M+H$^+$); calcd. for C$_{76}$H$_{104}$N$_{10}$O$_{36}$S: 1764.63 Da.

Embodiment 7: Preparing Compound 3

0.050 g (0.1 mmole) of simvastatin was dissolved in 10 ml of anhydrous tetrahydrofuran (THF) solution, and 0.1 ml (0.1 mmole) of isopropyl Grignard reagent was added and reacted for 64 hours. After removing the solvent by vacuum, colorless oil residue was obtained. It was partitioned between CH$_2$Cl$_2$ and brine. The aqueous layer was extracted by CH$_2$Cl$_2$ for 3 times, the combined organic layers were dried over MgSO$_4$ and filtered. After removing the solvent, white solid was obtained which is compound 3, and the yield was 36%, 0.055 g.

Embodiment 8: Preparing Compound 4

0.052 g (0.1 mmole) of simvastatin was dissolved in 10 ml of ethanol, and 1 mL of a NaOH solution (1 N) was added and reacted for 10 minutes under room temperature. After removing the ethanol, 0.1 N of HCl solution was added to reach pH 6, and then freeze-drying was performed to obtain a white solid. Acetone was added to the white solid to allow the NaCl to segregate out in solid form. After removing the supernatant and removing the solvent, 0.042 g of white solid was obtained and the yield was 80%.

$^1$H NMR (400 MHz, CDCl$_3$): • 5.95 (d, J=10 Hz, 1H), 5.75 (m, 1H), 5.47 (br, 1H), 5.33 (br, 1H), 4.17 (br, 1H), 3.67 (br, 1H), 2.40 (m, 3H), 2.22 (m, 2H), 1.92 (br, 2H), 1.543 (m, 5H), 1.30 (m, 2H), 1.08 (m, 11H), 0.86 (d, J=6 Hz, 3H), 0.80 (t, J=8 Hz, 3H).

Mass (ESI, m/z): 437 (M+H)$^+$.

Embodiment 9: Preparing Compound 5

0.102 g (0.2 mmole) of simvastatin and 0.025 g (0.2 mmole) of ethanolamine were dissolved in 5 mL of CH$_2$Cl$_2$, and 0.2 mL (1.9 mmole) of N-methylmorpholine was added and reacted for 4 hours under room temperature. After removing the solvent by vacuum, a crude product of yellow oil was obtained. The crude was dissolved in CH$_2$Cl$_2$ and put into a separating funnel, CH$_2$Cl$_2$ was further added until the total volume of CH$_2$Cl$_2$ reached 30 mL, and then 30 mL of brine was added. A partition was performed and the aqueous layer was extracted by CH$_2$Cl$_2$ for three times. To combine all the organic layers, anhydrous sodium sulfate was used to remove the water from the organic solution, and then the solid sodium sulphate and solvent were removed to obtain 0.091 g of white solid, which is compound 5 with a yield of 80%.

$^1$H NMR (400 MHz, CDCl$_3$): • 7.16 (t, J=6 Hz, 1H), 5.94 (d, J=9 Hz, 1H), 5.74 (q, J=4 and 6 Hz, 1H), 5.46 (br, 1H), 5.33 (br, 1H), 4.24 (m, 2H), 3.67 (m, 4H), 3.37 (m, 2H), 2.30 (m, 5H), 1.91 (m, 2H), 1.52 (m, 5H), 1.12 (m, 13H), 0.84 (d, J=7 Hz, 3H), 0.79 (t, J=7 Hz, 3H).

$^{13}$C-NMR (CDCl$_3$, 100 MHz): δ 178.4, 172.7, 133.0, 131.5, 129.4, 128.2, 71.8, 69.1, 68.2, 61.2, 43.5, 42.9, 42.7, 42.1, 37.5, 36.3, 34.8, 32.9, 30.4, 27.2, 24.7, 24.6, 24.2, 23.0, 13.8, 9.2.

Mass (ESI, m/z): 502 (M+Na)$^+$. HRMS cald. for C$_{27}$H$_{45}$NO$_6$Na: 502.3144; found: 502.3142.

Embodiment 10: Preparing Compound 6

The preparation is similar to that of compound 5, but ethanolamine was replaced with monopropanolamine (0.018 g, 0.2 mmole). The reaction time was 4 hours, and 0.101 g of a white solid was obtained with a yield of 86%.

$^1$H-NMR (400 MHz, CDCl$_3$): δ 6.95 (br, 1H), 5.96 (d, J=10 Hz, 1H), 5.76 (br, 1H), 5.48 (br, 1H), 5.38 (m, 1H), 4.19 (br, 1H), 3.75 (br, 1H), 3.63 (m, 3H), 3.38 (br, 2H), 2.31 (m, 5H), 1.92 (m, 2H), 1.69 (m, 2H), 1.53 (m, 5H), 1.13 (m, 13H), 0.85 (d, J=7 Hz, 3H), 0.80 (t, J=8 Hz, 7H).

$^{13}$C-NMR (CDCl$_3$, 100 MHz): δ 178.4, 172.8, 133.0, 131.5, 129.5, 128.2, 72.0, 69.3, 68.2, 59.4, 43.4, 43.0, 42.5, 37.7, 36.3, 36.1, 34.7, 33.0, 32.9, 31.9, 30.4, 27.2, 24.8, 24.1, 23.1, 13.9, 9.3.

Mass (ESI, m/z): 516 (M+Na)$^+$. HRMS cald. for C$_{28}$H$_{47}$NO$_6$Na: 516.3300; found: 516.3297.

Embodiment 11: Preparing Compound 7

The preparation is similar to that of compound 5, but ethanolamine was replaced with polyoxyethylene alkylamine (0.025 g, 0.2 mmole). The reaction time was 2 hours, and 0.113 g of a white solid was obtained with a yield of 90%.

$^1$H-NMR (400 MHz, CDCl$_3$): δ 7.14 (br, 1H), 5.95 (d, J=10 Hz, 1H), 5.75 (dd, J=6 and 6 Hz, 1H), 5.47 (br, 1H), 5.36 (m, 1H), 4.20 (br, 1H), 3.72 (m, 4H), 3.55 (m, 5H), 3.44 (m, 2H), 2.30 (m, 5H), 1.92 (m, 2H), 1.52 (m, 5H), 1.12 (m, 11H), 0.84 (d, J=7 Hz, 3H), 0.79 (t, J=8 Hz, 3H).

$^{13}$C-NMR (CDCl$_3$, 100 MHz): δ 178.3, 172.2, 133.0, 131.5, 129.4, 128.2, 72.2, 72.0, 69.5, 69.4, 68.2, 61.4, 43.3, 42.9, 42.5, 39.1, 37.6, 36.2, 34.7, 33.0, 30.4, 27.2, 24.7, 24.6, 24.2, 23.0, 13.8, 9.3.

Mass (ESI, m/z): 546 (M+Na)$^+$. HRMS cald. for C$_{29}$H$_{49}$NO$_7$Na: 546.3407; found: 546.3404.

Embodiment 12: Preparing Compound 8

0.051 g (0.1 mmole) of simvastatin was dissolved in 4 mL of ethanol, and 60 μL (5.0 mmole) of hydrazine was added and reacted for two days under room temperature. After removing the solvent, yellow oil was obtained as the crude product. The crude product was extracted, dried and concentrated followed the same procedures for previous derivatives. After removing the solvent, 0.038 g of white solid was obtained with a yield of 70%.

$^1$H NMR (400 MHz, CDCl$_3$): • • 5.98 (d, J=10 Hz, 1H), 5.77 (m, 1H), 5.49 (m 1H), 5.48 (br, 1H), 4.20 (br, 1H), 3.78 (m, 1H), 2.45 (br, 1H), 2.34 (m, 3H), 2.23 (d, J=10 Hz, 1H), 1.87 (m, 2H), 1.58 (m, 5H), 1.21 (m, 2H), 1.12 (m, 11H), 0.86 (d, J=7 Hz, 3H), 0.82 (t, J=8 Hz, 3H).

$^{13}$C NMR (100 MHz, CDCl$_3$) • •• • 178.6, 132.9, 131.4, 129.6, 128.3, 125.9, 72.1, 69.3, 68.1, 43.0, 42.3, 37.9, 35.7, 34.7, 33.3, 32.9, 30.3, 27.2, 24.8, 24.7, 23.8, 23.1, 13.9, 9.3.

Mass (ESI, m/z): 473 (M+Na)$^+$. HRMS cald. for C$_{25}$H$_{42}$N$_2$O$_5$Na: 473.2986; found: 473.2987.

Embodiment 13: Preparing Compound 9

0.051 g (0.1 mmole) of simvastatin and 11 μL (0.11 mmole) of 2-pyridinemethaneamine were dissolved in 12 mL 1,4-dioxane and reacted for 7 days at room temperature. Then the solvent was removed to obtain yellow oil. The oil was purified by a normal phase column, and the elution was collected and identified using thin layer chromatography. R$_f$=0.25 (CH$_2$Cl$_2$:CH$_3$OH=10:0.2) Compound 9 was obtained with a yield of 35%.

$^1$H NMR (400 MHz, CDCl$_3$): • • 8.51 (d, J=4 Hz, 1H), 7.68 (td, J=8 and 2 Hz, 1H), 7.27 (br, 1H), 7.21 (m, 2H), 6.97 (t, J=6 Hz, 1H), 5.98 (d, J=9 Hz, 1H), 5.78 (dd, J=6 Hz, 1H), 5.49 (t, J=3 Hz, 1H), 5.39 (qui, J=2 and 3 Hz, 1H), 4.69 (dd, J=6 Hz, 1H), 4.50 (dd, J=5 Hz, 1H), 4.25 (m, 1H), 3.80 (m, 1H), 2.43 (m, 4H), 2.23 (m, 1H), 1.94 (m, 2H), 1.56 (m, 7H), 1.14 (m, 11H), 0.87 (d, J=7 Hz, 3H), 0.82 (t, J=7 Hz, 3H).

$^{13}$C NMR (100 MHz, CDCl$_3$): • • 178.1, 172.3, 156.2, 148.9, 137.0, 133.2, 131.7, 129.5, 128.3, 122.5, 122.0, 72.3, 69.9, 68.1, 44.2, 43.8, 43.0, 42.5, 37.7, 36.2, 34.7, 33.0, 30.5, 27.3, 24.8, 24.2, 23.1, 13.9, 9.3.

Embodiment 14: Preparing Compound 10

0.051 g (0.1 mmole) of simvastatin and 18 μL (0.3 mmole) of propylamine were mixed in 12 mL of THF and reacted for 7 days under room temperature. Then the solvent was removed to obtain yellow oil. The oil was purified using a normal phase column, and the elution was collected and identified using thin layer chromatography. R$_f$=0.25 (CH$_2$Cl$_2$:CH$_3$OH=8:0.2) Compound 10 was obtained with a yield of 48%.

$^1$H NMR (400 MHz, CDCl$_3$): • • 6.28 (br, 1H), 5.98 (d, J=10 Hz, 1H), 5.83 (m, 2H), 5.49 (br, 1H), 5.43 (q, J=3 Hz, 1H), 5.17 (m, 1H), 4.72 (br, 1H), 4.21 (qua, J=5 and 7 Hz, 1H), 3.89 (t, J=4 Hz, 2H), 3.79 (m, 1H), 3.62 (br, 1H), 2.39 (m, 4H), 2.23 (m, 1H), 1.79 (m, 2H), 1.56 (m, 7H), 1.08 (m, 11H), 0.86 (d, J=7 Hz, 3H), 0.82 (t, J=7 Hz, 3H).

$^{13}$C NMR (100 MHz, CDCl$_3$): • • 178.4, 171.7, 134.0, 133.0, 131.4, 129.6, 128.2, 116.4, 72.3, 69.6, 68.1, 43.0, 42.9, 42.3, 41.7, 37.9, 35.8, 34.6, 33.2, 32.9, 30.3, 27.2, 24.8, 24.7, 23.9, 23.1, 13.9, 9.3.

Mass (ESI, m/z): 498 (M+Na)$^+$. HRMS cald. for C$_{28}$H$_{45}$NO$_5$Na: 498.3190; found: 498.3189.

Embodiment 15: Preparing Compound 11

0.051 g (0.1 mmole) of simvastatin and 18 μL (0.3 mmole) of propylamine were mixed in 12 mL of THF and reacted for 7 days at room temperature. Then the solvent was removed to obtain yellow oil. The oil was separated using a normal phase column, and the elution was collected and identified using thin layer chromatography. R$_f$=0.3 (CH$_2$Cl$_2$:CH$_3$OH=10:0.2) Compound 11 was obtained with a yield of 60%.

$^1$H NMR (400 MHz, CDCl$_3$): • 6.23 (t, J=3 Hz, 1H), 5.97 (d, J=10 Hz, 1H), 5.76 (dd, J=4 and 6 Hz, 1H), 5.48 (br, 1H), 5.40 (qui, J=2 and 3 Hz, 1H), 4.80 (br 1H), 4.19 (m, 1H), 3.74 (m, 2H), 3.21 (m, 2H), 2.27 (m, 5H), 1.93 (m, 2H), 1.54 (m, 7H), 1.15 (m, 11H), 0.94 (t, J=7 Hz, 3H), 0.83 (m, 6H).

$^{13}$C NMR (100 MHz, CDCl$_3$): • • • 178.3, 171.9, 133.0, 131.5, 129.5, 128.2, 72.3, 69.6, 68.1, 43.0, 42.3, 41.0, 37.8, 35.9, 34.6, 33.1, 32.9, 30.4, 27.2, 24.8, 24.6, 24.0 23.1, 22.7, 13.9, 11.3, 9.3.

Mass (ESI, m/z): 500 (M+Na)$^+$. HRMS cald. for C$_{28}$H$_{47}$NO$_5$Na: 500.3346; found: 500.3348.

EMBODIMENTS

1. A method for treating low bone mineral density associated with osteopenia, osteoporosis, and other diseases, comprising:

administrating a composition comprising a 3,5-dihydroxypentanoic acid derivative according to Formula I to a vertebrate,

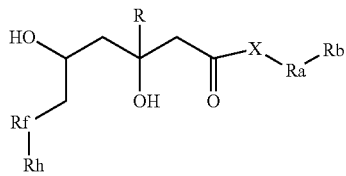

Formula I wherein X is one of nitrogen and carbon;

R is one of hydrogen and a C$_1$-C$_4$ alkyl group;

Ra is one group selected from the following groups: (a1) a C$_1$-C$_{10}$ alkyl group, (a2) a substituted C$_1$-C$_{10}$ alkyl group, (a3) a C$_3$-C$_8$ cycloalkyl group, (a4) a substituted C$_3$-C$_8$ cycloalkyl group, (a5) a phenylamino group, (a6) a substituted phenylamino group, (a7) a C$_1$-C$_{10}$ phenyl alkylamino group, (a8) a substituted C$_1$-C$_{10}$ phenyl alkylamino group, (a9) a bisphosphonate, (a10) tetracycline, (a11) an amino acid, (a12) an acidic oligopeptide, (a13) a bone-targeting peptide and (a14) a bone affinity peptide, U-Lys(U)-Lys(U)-Gly-OH, wherein U is one selected from the group consisting of -Lys, -Lys-(Asp-NHAc)$_J$, —NHAc, -Lys-(Asp-)$_K$-NHAc and (Asp-NHAc)$_J$, wherein J is 1 or 2, and K is an integer, 1≤K≤20;

Rb is one selected from the group consisting of hydrogen, a substituted group, an acetyl group and an imaging moiety;

The bond between Rf and Rh are single- or a double bond;

Rh is one selected from the group consisting of compounds represented by Formulae (A), (B), (C), (D), (E) and (F)

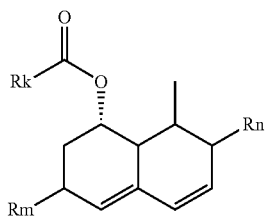

Formula (A)

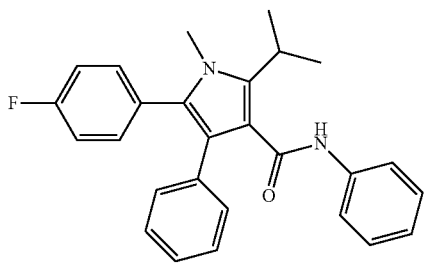

Formula (B)

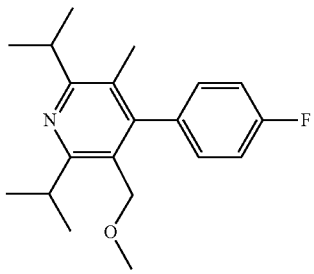

Formula (C)

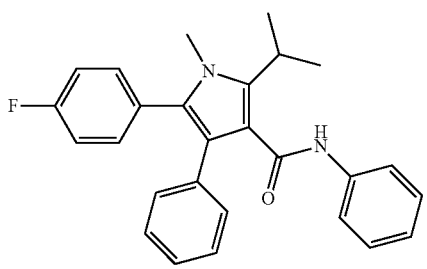

Formula (D)

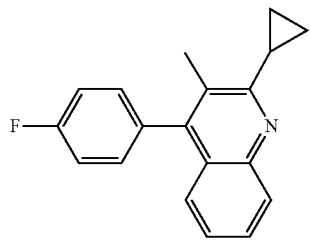

Formula (E)

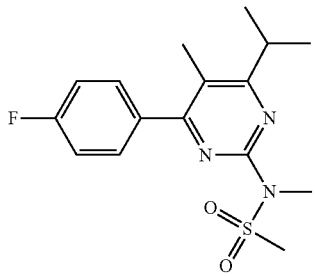

Formula (F)

Rk is a C$_1$-C$_5$ alkyl group;

Rm is one of C$_1$-C$_5$ alkyl groups and a hydroxyl group; and

Rn is one of C$_1$-C$_5$ alkyl groups and a hydroxyl group.

2. The method of Embodiment 1, wherein Ra is (a2) a substituted C$_1$-C$_{10}$ alkyl group, and the substituted group is one selected from the group consisting of a C$_1$-C$_{10}$ alkyl group, a C$_1$-C$_{10}$ alkoxy group, a C$_1$-C$_5$ alkoxycarbonyl group, a C$_1$-C$_5$ acyloxy group, a C$_3$-C$_8$ cycloalkyl group, a phenyl group and a substituted phenyl group.

3. The method of Embodiments 1-2, wherein Ra is one selected from the group consisting of (a4) a substituted $C_3$-$C_8$ cycloalkyl group, (a6) a substituted phenylamino group and (a8) a substituted phenyl $C_1$-$C_{10}$ alkylamino group, and the substituent is one selected from the group consisting of a $C_1$-$C_5$ alkyl group, fluorine, chlorine, bromine, iodine, furan, a six-member aromatic ring with at least one oxygen atom, pyrrole and pyridine.

4. The method of Embodiments 1-3, wherein Ra is (a12) acidic oligopeptides and is one selected from the group consisting of -Lys-(Asp)$_m$-Lys-PEG, Asp$_m$ and Glu$_n$, wherein m and n are both integers from 1 to 10, inclusive, each Asp residue is one of D-Asp and L-Asp, and each Glu residue is one of D-Glu and L-Glu.

5. The method of Embodiments 1-4, wherein Ra is (a13) bone-targeting peptide which is one selected from the group consisting of

```
                                          (SEQ ID NO: 1)
Thr-Met-Arg-Asn-Pro-Ile-Thr-Ser-Leu-Ile-Ser-Val, (SEQ ID NO: 2)
Leu-Leu-Ala-Asp-Thr-Thr-His-His-Arg-Pro-Trp-Thr-
Gly-Gly-Gly-Ser, (SEQ ID NO: 3)
Lys-Glu-Ile-Pro-Pro-Ile-Pro-Leu-Leu-Ala-Pro-Ser-
Gly-Gly-Gly-Ser, (SEQ ID NO: 4)
Asn-Asn-Val-Ser-Gln-Lys-Trp-Gln-Gln-Arg-Leu-Ile-
Gly-Gly-Gly-Ser, (SEQ ID NO: 5)
Asn-Ser-Met-Ile-Ala-His-Asn-Lys-Thr-Arg-Met-His-
Gly-Gly-Gly-Ser, (SEQ ID NO: 6)
Gly-Ile-His-Val-Pro-Trp-Met-Pro-Pro-Val-Ala-Phe-
Gly-Gly-Gly-Ser, (SEQ ID NO: 7)
Gln-Arg-Ser-Trp-Thr-Leu-Asp-Ser-Ala-Leu-Ser-Met-
Gly-Gly-Glu-Ser, (SEQ ID NO: 8)
Ser-Gly-His-Gln-Leu-Leu-Leu-Asn-Lys-Met-Pro-Asn-
Gly-Gly-Gly-Ser, (SEQ ID NO: 9)
Ser-Ser-Thr-Leu-Lys-Thr-Phe-Phe-Gly-Phe-Pro-Asp-
Gly-Gly-Gly-Ser, (SEQ ID NO: 10)
Asp-Ser-Ser-Asn-Pro-Ile-Phe-Trp-Arg-Pro-Ser-Ser-
Gly-Gly-Gly-Ser, (SEQ ID NO: 11)
Asn-Thr-Ser-His-Leu-Arg-Val-Lys-Leu-Pro-Thr-Pro-
Gly-Gly-Gly-Ser, (SEQ ID NO: 12)
Ser-Gly-His-Gln-Leu-Leu-Leu-Asn-Lys-Met-Pro-Asn-
Gly-Gly-Gly-Ser, (SEQ ID NO: 13)
Ala-Thr-Trp-Ser-His-His-Leu-Ser-Ser-Ala-Gly-Leu-
Gly-Gly-Gly-Ser, (SEQ ID NO: 14)
Ser-Tyr-Ser-Gln-Met-Asp-Pro-Pro-Arg-Ser-Leu-Pro-
Gly-Gly-Gly-Ser, (SEQ ID NO: 15)
Thr-Met-Arg-Asn-Pro-Ile-Thr-Ser-Leu-Ile-Ser-Val, (SEQ ID NO: 16)
Leu-Leu-Ala-Asp-Thr-Thr-His-His-Arg-Pro-Trp-Thr, (SEQ ID NO: 17)
Lys-Glu-Ile-Pro-Pro-Ile-Pro-Leu-Leu-Ala-Pro-Ser, (SEQ ID NO: 18)
Asn-Asn-Val-Ser-Gln-Lys-Trp-Gln-Gln-Arg-Leu-Ile, (SEQ ID NO: 19)
Asn-Ser-Met-Ile-Ala-His-Asn-Lys-Thr-Arg-Met-His, (SEQ ID NO: 20)
Gly-Ile-His-Val-Pro-Trp-Met-Pro-Pro-Val-Ala-Phe, (SEQ ID NO: 21)
Gln-Arg-Ser-Trp-Thr-Leu-Asp-Ser-Ala-Leu-Ser-Met, (SEQ ID NO: 22)
Ser-Gly-His-Gln-Leu-Leu-Leu-Asn-Lys-Met-Pro-Asn, (SEQ ID NO: 23)
Ser-Ser-Thr-Leu-Lys-Thr-Phe-Phe-Gly-Phe-Pro-Asp, (SEQ ID NO: 24)
Asp-Ser-Ser-Asn-Pro-Ile-Phe-Trp-Arg-Pro-Ser-Ser, (SEQ ID NO: 25)
Asn-Tyr-Ser-His-Leu-Arg-Val-Lys-Leu-Pro-Thr-Pro, (SEQ ID NO: 26)
Ser-Gly-His-Gln-Leu-Leu-Leu-Asn-Lys-Met-Pro-Asn, (SEQ ID NO: 27)
Ala-Thr-Trp-Ser-His-His-Leu-Ser-Ser-Ala-Gly-Leu,
and
                                          (SEQ ID NO: 28)
Ser-Tyr-Ser-Gln-Met-Asp-Pro-Pro-Arg-Ser-Leu-Pro-
Gly-Gly-Gly-Ser.
```

6. The method of Embodiments 1-5, wherein Ra is (a14) U-Lys(U)-Lys(U)-Gly-OH.

7. The method of Embodiments 1-6, wherein the composition is one of a pharmaceutical composition and a food composition.

8. A derivative of 3,5-dihydroxypentanoic acid having a structure according to Formula I,

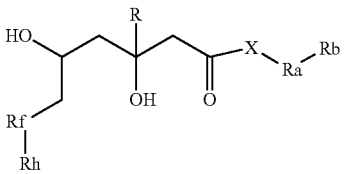

Formula I wherein X is one of nitrogen and carbon;

R is one of hydrogen and $C_1$-$C_4$ alkyl group;

Ra is one group selected from the following groups: (a1) a $C_1$-$C_{10}$ alkyl group, (a2) a substituted $C_1$-$C_{10}$ alkyl group, (a3) a $C_3$-$C_8$ cycloalkyl group, (a4) a substituted $C_3$-$C_8$ cycloalkyl group, (a5) a phenylamino group, (a6) a substituted phenylamino group, (a7) a $C_1$-$C_{10}$ phenyl alkylamino group, (a8) a substituted $C_1$-$C_{10}$ phenyl alkylamino group, (a9) a bisphosphonate, (a10) tetracycline, (a11) an amino acid, (a12) an acidic oligopeptide, (a13) a bone-targeting peptide and (a14) a bone affinity peptide, U-Lys(U)-Lys(U)-Gly-OH, wherein U is one selected from the group consisting of -Lys, -Lys-(Asp-NHAc)$_J$, —NHAc, -Lys-(Asp-)$_K$-NHAc and (Asp-NHAc)$_J$, wherein J is 1 or 2, and K is an integer, $1 \leq K \leq 20$;

Rb is one selected from the group consisting of hydrogen, a substituted group, an acetyl group and an imaging moiety;

The bond between Rf and Rh are single- or a double bond;

Rh is one selected from the group consisting of compounds represented by Formulae (A), (B), (C), (D), (E) and (F), Formula (A)
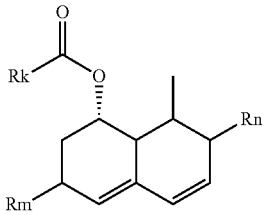

Formula (B)
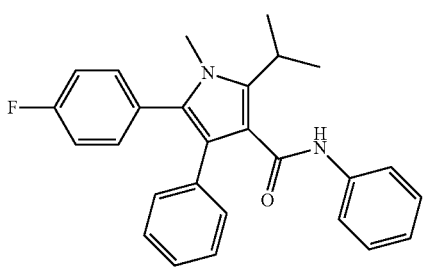

Formula (C)
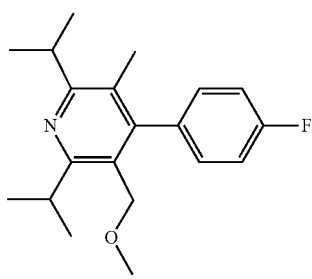

Formula (D)
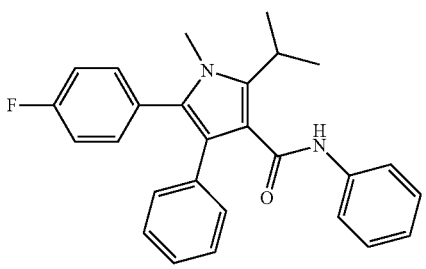

Formula (E)
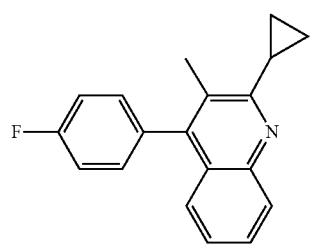

Formula (F)
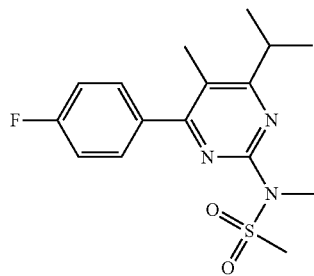

Rk is a $C_1$-$C_5$ alkyl group;

Rm is one of $C_1$-$C_5$ alkyl groups and a hydroxyl group; and

Rn is one of $C_1$-$C_5$ alkyl groups and a hydroxyl group.

9. The compound of Embodiment 8, wherein Ra is (a2) a substituted $C_1$-$C_{10}$ alkyl group, and the substituted group is one selected from the group consisting of a $C_1$-$C_{10}$ alkyl group, a $C_1$-$C_{10}$ alkoxy group, a $C_1$-$C_5$ alkoxycarbonyl group, a $C_1$-$C_5$ acyloxy group, a $C_3$-$C_8$ cycloalkyl group, a phenyl group and a substituted phenyl group.

10. The compound of Embodiments 8-9, wherein Ra is one selected from the group consisting of (a4) a substituted cycloalkyl group with $C_3$-$C_8$, (a6) a substituted phenylamino group and (a8) a substituted phenyl alkylamino group with $C_1$-$C_{10}$, and the substituted group is one selected from the group consisting of an alkyl group with $C_1$-$C_5$, fluorine, chlorine, bromine, iodine, furan, a six-member aromatic ring with at least one oxygen atom, pyrrole and pyridine.

11. The compound of Embodiments 8-10, wherein Ra is (a12) acidic oligopeptides and is one selected from the group consisting of -Lys-(Asp)$_m$-Lys-PEG, Asp$_m$ and Glu$_n$, wherein m and n are both integers from 1 to 10, inclusive, each Asp residue is one of D-Asp and L-Asp, and each Glu residue is one of D-Glu and L-Glu.

12. The compound of Embodiments 8-11, wherein Ra is (a13) bone-targeting peptide which is one selected from the group consisting of

```
                                        (SEQ ID NO: 1)
Thr-Met-Arg-Asn-Pro-Ile-Thr-Ser-Leu-Ile-Ser-Val, (SEQ ID NO: 2)
Leu-Leu-Ala-Asp-Thr-Thr-His-His-Arg-Pro-Trp-Thr-
Gly-Gly-Gly-Ser, (SEQ ID NO: 3)
Lys-Glu-Ile-Pro-Pro-Ile-Pro-Leu-Leu-Ala-Pro-Ser-
Gly-Gly-Gly-Ser, (SEQ ID NO: 4)
Asn-Asn-Val-Ser-Gln-Lys-Trp-Gln-Gln-Arg-Leu-Ile-
Gly-Gly-Gly-Ser, (SEQ ID NO: 5)
Asn-Ser-Met-Ile-Ala-His-Asn-Lys-Thr-Arg-Met-His-
Gly-Gly-Gly-Ser, (SEQ ID NO: 6)
Gly-Ile-His-Val-Pro-Trp-Met-Pro-Pro-Val-Ala-Phe-
Gly-Gly-Gly-Ser, (SEQ ID NO: 7)
Gln-Arg-Ser-Trp-Thr-Leu-Asp-Ser-Ala-Leu-Ser-Met-
Gly-Gly-Glu-Ser,
```

(SEQ ID NO: 8)
Ser-Gly-His-Gln-Leu-Leu-Asn-Lys-Met-Pro-Asn-Gly-Gly-Gly-Ser, (SEQ ID NO: 9)
Ser-Ser-Thr-Leu-Lys-Thr-Phe-Phe-Gly-Phe-Pro-Asp-Gly-Gly-Gly-Ser, (SEQ ID NO: 10)
Asp-Ser-Ser-Asn-Pro-Ile-Phe-Trp-Arg-Pro-Ser-Ser-Gly-Gly-Gly-Ser, (SEQ ID NO: 11)
Asn-Thr-Ser-His-Leu-Arg-Val-Lys-Leu-Pro-Thr-Pro-Gly-Gly-Gly-Ser, (SEQ ID NO: 12)
Ser-Gly-His-Gln-Leu-Leu-Leu-Asn-Lys-Met-Pro-Asn-Gly-Gly-Gly-Ser, (SEQ ID NO: 13)
Ala-Thr-Trp-Ser-His-His-Leu-Ser-Ser-Ala-Gly-Leu-Gly-Gly-Gly-Ser, (SEQ ID NO: 14)
Ser-Tyr-Ser-Gln-Met-Asp-Pro-Pro-Arg-Ser-Leu-Pro-Gly-Gly-Gly-Ser, (SEQ ID NO: 15)
Thr-Met-Arg-Asn-Pro-Ile-Thr-Ser-Leu-Ile-Ser-Val, (SEQ ID NO: 16)
Leu-Leu-Ala-Asp-Thr-Thr-His-His-Arg-Pro-Trp-Thr, (SEQ ID NO: 17)
Lys-Glu-Ile-Pro-Pro-Ile-Pro-Leu-Leu-Ala-Pro-Ser, (SEQ ID NO: 18)
Asn-Asn-Val-Ser-Gln-Lys-Trp-Gln-Gln-Arg-Leu-Ile, (SEQ ID NO: 19)
Asn-Ser-Met-Ile-Ala-His-Asn-Lys-Thr-Arg-Met-His, (SEQ ID NO: 20)
Gly-Ile-His-Val-Pro-Trp-Met-Pro-Pro-Val-Ala-Phe, (SEQ ID NO: 21)
Gln-Arg-Ser-Trp-Thr-Leu-Asp-Ser-Ala-Leu-Ser-Met, (SEQ ID NO: 22)
Ser-Gly-His-Gln-Leu-Leu-Leu-Asn-Lys-Met-Pro-Asn, (SEQ ID NO: 23)
Ser-Ser-Thr-Leu-Lys-Thr-Phe-Phe-Gly-Phe-Pro-Asp, (SEQ ID NO: 24)
Asp-Ser-Ser-Asn-Pro-Ile-Phe-Trp-Arg-Pro-Ser-Ser, (SEQ ID NO: 25)
Asn-Tyr-Ser-His-Leu-Arg-Val-Lys-Leu-Pro-Thr-Pro, (SEQ ID NO: 26)
Ser-Gly-His-Gln-Leu-Leu-Leu-Asn-Lys-Met-Pro-Asn, (SEQ ID NO: 27)
Ala-Thr-Trp-Ser-His-His-Leu-Ser-Ser-Ala-Gly-Leu, and (SEQ ID NO: 28)
Ser-Tyr-Ser-Gln-Met-Asp-Pro-Pro-Arg-Ser-Leu-Pro-Gly-Gly-Gly-Ser.

13. The compound of Embodiments 8-12, wherein Ra is (a14) U-Lys(U)-Lys(U)-Gly-OH.

14. A compound having a structure according to Formula II,

Formula II wherein Rt is one selected from the group consisting of a $C_1$-$C_{10}$ alkyl group, a hydroxyl group, a $C_1$-$C_{10}$ alkylamino group, —NH—($C_1$-$C_{10}$)alkyl-Rz, —NH—($C_1$-$C_5$)alkyl-O—($C_1$-$C_5$)alkyl-Rz, —NH-amino group; and Rz is one selected from the group consisting of a $C_1$-$C_{10}$ unsaturated alkyl group, a hydroxyl group, an amino group, furan, a six-member aromatic ring with at least one oxygen atom, pyrrole and pyridine.

Based on the above, the present invention effectively solves the problems and drawbacks in the prior art, and thus it meets the demands of the industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

Reference: *Organic Letters* 2014 16 (17), 4376-4379 A novel anabolic agent: a simvastatin analogue without HMG-CoA reductase inhibitory activity

What is claimed is:

1. A method for treating low bone mineral density associated with osteopenia, osteoporosis, and other diseases, comprising:

administrating a composition comprising a 3,5-dihydroxypentanoic acid derivative according to Formula I to a mammal,

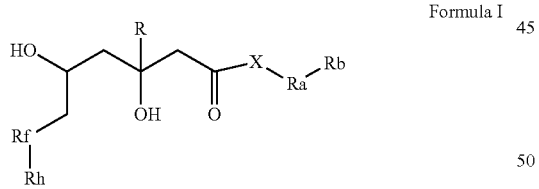

Formula I wherein X is one of nitrogen and carbon;
R is one of hydrogen and $C_1$-$C_4$ alkyl group;
Ra is one group selected from the following groups: (a1) a $C_1$-$C_{10}$ alkyl group, (a2) a $C_1$-$C_{10}$ alkyl group, (a3) a $C_3$-$C_8$ cycloalkyl group, (a4) a $C_3$-$C_8$ cycloalkyl group, (a5) a phenylamino group, (a6) a phenylamino group, (a7) a $C_1$-$C_{10}$ phenyl alkylamino group, (a8) a $C_1$-$C_{10}$ phenyl alkylamino group, (a9) a bisphosphonate, (a10) tetracycline, (a11) an amino acid, (a12) an acidic oligopeptide, (a13) a bone-targeting peptide and (a14) a bone affinity peptide, U-Lys(U)-Lys(U)-Gly-OH, wherein U is one selected from the group consisting of -Lys, -Lys-(Asp-NHAc)$_J$, —NHAc, -Lys-(Asp-)$_K$-NHAc and (Asp-NHAc)$_J$, wherein J is 1 or 2, and K is an integer, $1 \leq K \leq 20$;

Rb is one of hydrogen and an acetyl group;
the bond between Rf and Rh are single- or a double bond;
Rh is one selected from the group consisting of compounds represented by Formulae (A), (B), (C), (D), (E) and (F),

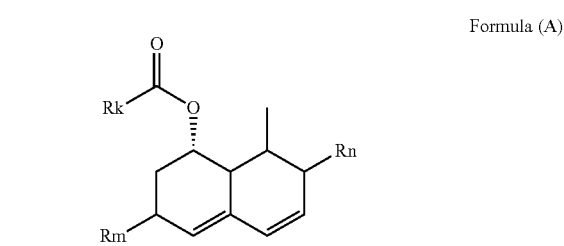

Formula (A)

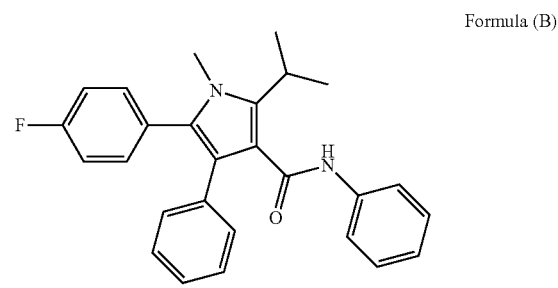

Formula (B)

Formula (C)

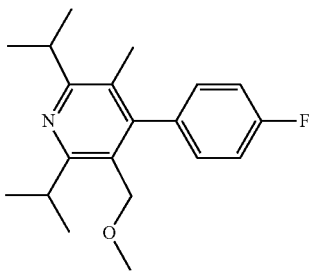

Formula (D)

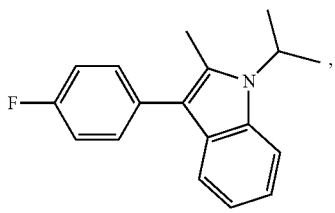

Formula (E)

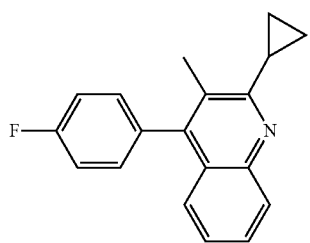

Formula (F)

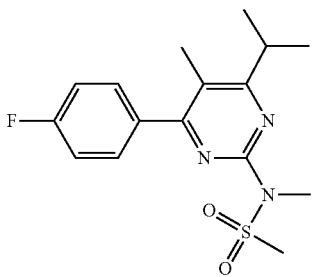

Rk is a $C_1$-$C_5$ alkyl group;
Rm is one of $C_1$-$C_5$ alkyl groups and a hydroxyl group;
Rf is a carbon atom;
Rn is one of $C_1$-$C_5$ alkyl groups and a hydroxyl group; and
the 3,5-dihydroxypentanoic acid derivative according to Formula I is irrelevant to

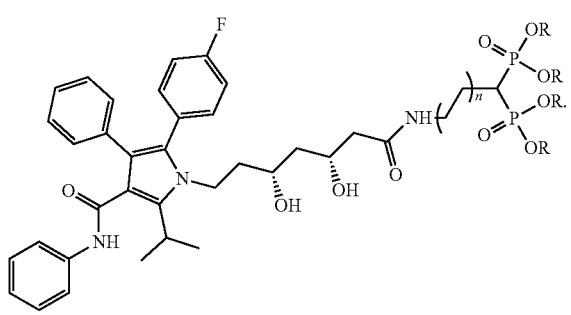

2. The method as claimed in claim 1, wherein Ra is (a2) a substituted $C_1$-$C_{10}$ alkyl group, and the substituted group is one selected from the group consisting of a $C_1$-$C_{10}$ alkyl group, a $C_1$-$C_{10}$ alkoxy group, a $C_1$-$C_5$ alkoxycarbonyl group, a $C_1$-$C_5$ acyloxyl group, a $C_3$-$C_8$ cycloalkyl group, a phenyl group and a substituted phenyl group.

3. The method as claimed in claim 1, wherein Ra is one selected from the group consisting of (a4) a substituted cycloalkyl group with $C_3$-$C_8$, (a6) a substituted phenylamino group and (a8) a substituted phenyl alkylamino group with $C_1$-$C_{10}$, and the substituted group is one selected from the group consisting of an alkyl group with $C_1$-$C_5$, fluorine, chlorine, bromine, iodine, furan, a six-member aromatic ring with at least one oxygen atom, pyrrole and pyridine.

4. The method as claimed in claim 1, wherein Ra is (a12) acidic oligopeptides and is one selected from the group consisting of -Lys-(Asp)$_m$-Lys-PEG, Asp$_m$ and Glu$_n$, wherein m and n are both integers from 1 to 10, inclusive, each Asp residue is one of D-Asp and L-Asp, and each Glu residue is one of D-Glu and L-Glu.

5. The method as claimed in claim 1, wherein Ra is (a13) bone-targeting peptide which is one selected from the group consisting of Thr-Met-Arg-Asn-Pro-Ile-Thr-Ser-Leu-Ile-Ser-Val, Leu-Leu-Ala-Asp-Thr-Thr-His-His-Arg-Pro-Trp-Thr-Gly-Gly-Gly-Ser, Lys-Glu-Ile-Pro-Pro-Ile-Pro-Leu-Leu-Ala-Pro-Ser-Gly-Gly-Gly-Ser, Asn-Asn-Val-Ser-Gln-Lys-Trp-Gln-Gln-Arg-Leu-Ile-Gly-Gly-Gly-Ser, Asn-Ser-Met-Ile-Ala-His-Asn-Lys-Thr-Arg-Met-His-Gly-Gly-Gly-Ser, Gly-Ile-His-Val-Pro-Trp-Met-Pro-Pro-Val-Ala-Phe-Gly-Gly-Gly-Ser, Gln-Arg-Ser-Trp-Thr-Leu-Asp-Ser-Ala-Leu-Ser-Met-Gly-Gly-Glu-Ser, Ser-Gly-His-Gln-Leu-Leu-Leu-Asn-Lys-Met-Pro-Asn-Gly-Gly-Gly-Ser, Ser-Ser-Thr-Leu-Lys-Thr-Phe-Phe-Gly-Phe-Pro-Asp-Gly-Gly-Gly-Ser, Asp-Ser-Ser-Asn-Pro-Ile-Phe-Trp-Arg-Pro-Ser-Ser-Gly-Gly-Gly-Ser, Asn-Thr-Ser-His-Leu-Arg-Val-Lys-Leu-Pro-Thr-Pro-Gly-Gly-Gly-Ser, Ser-Gly-His-Gln-Leu-Leu-Leu-Asn-Lys-Met-Pro-Asn-Gly-Gly-Gly-Ser, Ala-Thr-Trp-Ser-His-His-Leu-Ser-Ser-Ala-Gly-Leu-Gly-Gly-Gly-Ser, Ser-Tyr-Ser-Gln-Met-Asp-Pro-Pro-Arg-Ser-Leu-Pro-Gly-Gly-Gly-Ser, Thr-Met-Arg-Asn-Pro-Ile-Thr-Ser-Leu-Ile-Ser-Val, Leu-Leu-Ala-Asp-Thr-Thr-His-His-Arg-Pro-Trp-Thr, Lys-Glu-Ile-Pro-Pro-Ile-Pro-Leu-Leu-Ala-Pro-Ser, Asn-Asn-Val-Ser-Gln-Lys-Trp-Gln-Gln-Arg-Leu-Ile, Asn-Ser-Met-Ile-Ala-His-Asn-Lys-Thr-Arg-Met-His, Gly-Ile-His-Val-Pro-Trp-Met-Pro-Pro-Val-Ala-Phe, Gln-Arg-Ser-Trp-Thr-Leu-Asp-Ser-Ala-Leu-Ser-Met, Ser-Gly-His-Gln-Leu-Leu-Leu-Asn-Lys-Met-Pro-Asn, Ser-Ser-Thr-Leu-Lys-Thr-Phe-Phe-Gly-Phe-Pro-Asp, Asp-Ser-Ser-Asn-Pro-Ile-Phe-Trp-Arg-Pro-Ser-Ser, Asn-Tyr-Ser-His-Leu-Arg-Val-Lys-Leu-Pro-Thr-Pro, Ser-Gly-His-Gln-Leu-Leu-Leu-Asn-Lys-Met-Pro-Asn, Ala-Thr-Trp-Ser-His-His-Leu-Ser-Ser-Ala-Gly-Leu, and Ser-Tyr-Ser-Gln-Met-Asp-Pro-Pro-Arg-Ser-Leu-Pro-Gly-Gly-Gly-Ser.

6. The method as claimed in claim 1, wherein Ra is (a14) U-Lys(U)-Lys(U)-Gly-OH.

7. The method as claimed in claim 1, wherein the composition is one of a pharmaceutical composition and a food composition.

* * * * *